(12) United States Patent
Moriya et al.

(10) Patent No.: US 11,701,648 B2
(45) Date of Patent: Jul. 18, 2023

(54) METHOD FOR PRODUCING CATALYST FOR AMMOXIDATION, AND METHOD FOR PRODUCING ACRYLONITRILE

(71) Applicant: ASAHI KASEI KABUSHIKI KAISHA, Tokyo (JP)

(72) Inventors: Kohei Moriya, Tokyo (JP); Akiyoshi Fukuzawa, Tokyo (JP)

(73) Assignee: ASAHI KASEI KABUSHIKI KAISHA, Tokyo (JP)

( * ) Notice: Subject to any disclaimer, the term of this patent is extended or adjusted under 35 U.S.C. 154(b) by 275 days.

(21) Appl. No.: 17/270,281

(22) PCT Filed: Aug. 13, 2019

(86) PCT No.: PCT/JP2019/031835
§ 371 (c)(1),
(2) Date: Feb. 22, 2021

(87) PCT Pub. No.: WO2020/039998
PCT Pub. Date: Feb. 27, 2020

(65) Prior Publication Data
US 2021/0316292 A1    Oct. 14, 2021

(30) Foreign Application Priority Data

Aug. 23, 2018  (JP) ................. 2018-156514

(51) Int. Cl.
| | | |
|---|---|---|
| *B01J 37/00* | (2006.01) | |
| *B01J 37/08* | (2006.01) | |
| *B01J 35/00* | (2006.01) | |
| *B01J 35/02* | (2006.01) | |
| *B01J 23/887* | (2006.01) | |
| *B01J 21/08* | (2006.01) | |
| *C07C 253/26* | (2006.01) | |

(52) U.S. Cl.
CPC .......... *B01J 37/0045* (2013.01); *B01J 21/08* (2013.01); *B01J 23/8876* (2013.01); *B01J 35/0026* (2013.01); *B01J 35/023* (2013.01); *B01J 37/088* (2013.01); *C07C 253/26* (2013.01)

(58) Field of Classification Search
CPC .............. B01J 37/0045; B01J 37/088; B01J 35/0026; B01J 35/023; B01J 23/8876; B01J 21/08
See application file for complete search history.

(56) References Cited

U.S. PATENT DOCUMENTS

| 4,278,614 | A | 7/1981 | Umemura et al. |
|---|---|---|---|
| 6,740,769 | B1 | 5/2004 | Mizutani et al. |
| 2003/0088118 | A1 | 5/2003 | Komada et al. |
| 2006/0155139 | A1 | 7/2006 | Yanagi et al. |
| 2011/0233460 | A1 | 9/2011 | Brazdil et al. |
| 2012/0296108 | A1 | 11/2012 | Raichle et al. |
| 2016/0279618 | A1 | 9/2016 | Lugmair et al. |
| 2018/0085737 | A1 | 3/2018 | Miike et al. |
| 2018/0318803 | A1 | 11/2018 | Fukuzawa et al. |
| 2019/0091666 | A1 | 3/2019 | Aiki et al. |
| 2019/0126262 | A1 | 5/2019 | Aiki et al. |
| 2019/0168191 | A1 | 6/2019 | Aiki et al. |

FOREIGN PATENT DOCUMENTS

| CN | 1361719 A | 7/2002 |
|---|---|---|
| CN | 1174801 C | 11/2004 |
| CN | 106478457 A | 3/2017 |
| CN | 107614102 A | 1/2018 |
| EP | 2 700 447 A1 | 2/2014 |
| JP | 2002-45693 A | 2/2002 |
| JP | 2004-105951 A | 4/2004 |
| JP | 2006-263715 A | 10/2006 |
| JP | 4425743 B2 | 3/2010 |
| JP | 2010-131575 A | 6/2010 |
| JP | 2010-172851 A | 8/2010 |
| JP | 2010-240593 A | 10/2010 |
| JP | 4823950 B2 | 11/2011 |
| JP | 2012-501839 A | 1/2012 |
| JP | 4954750 B2 | 6/2012 |
| JP | 2012-245484 A | 12/2012 |
| JP | 2013-527141 A | 6/2013 |
| JP | 5378041 B2 | 12/2013 |
| JP | 5491037 B2 | 5/2014 |
| JP | 2015-188801 A | 11/2015 |
| JP | 2015-188801 A * | 11/2015 |
| JP | 5919870 B2 | 5/2016 |
| KR | 10-2018-0088363 A | 8/2018 |
| RU | 2612976 C2 | 3/2017 |
| SU | 957763 A | 9/1982 |
| TW | I264327 B | 10/2006 |
| WO | WO 2013/043371 A1 | 3/2013 |

(Continued)

OTHER PUBLICATIONS

International Search Report for PCT/JP2019/031835 dated Oct. 29, 2019.
Written Opinion of the International Searching Authority for PCT/JP2019/031835 (PCT/ISA/237) dated Oct. 29, 2019.
Supplementary European Search Report dated May 14, 2021, in European Patent Application No. 19851415.0.
English translation of International Preliminary Report on Patentability and Written Opinion dated Mar. 4, 2021, in PCT/JP2019/031835.

*Primary Examiner* — Yong L Chu
(74) *Attorney, Agent, or Firm* — Birch, Stewart, Kolasch & Birch, LLP

(57) ABSTRACT

The present invention provides a method for producing a catalyst for ammoxidation, comprising steps of: preparing a catalyst precursor slurry comprising a liquid phase and a solid phase; drying the catalyst precursor slurry to obtain dry a particle; and calcining the dry particle to obtain a catalyst for ammoxidation, wherein the solid phase of the catalyst precursor slurry comprises an aggregate containing a metal and a carrier, metal primary particles constituting the aggregate have a particle size of 1 μm or smaller, and an average particle size of the metal primary particles is 40 nm or larger and 200 nm or smaller.

22 Claims, 1 Drawing Sheet

(56) References Cited

FOREIGN PATENT DOCUMENTS

| WO | WO 2016/159085 A1 | 10/2016 |
| WO | WO 2017/217343 A1 | 12/2017 |
| WO | WO 2018/043007 A1 | 3/2018 |

\* cited by examiner

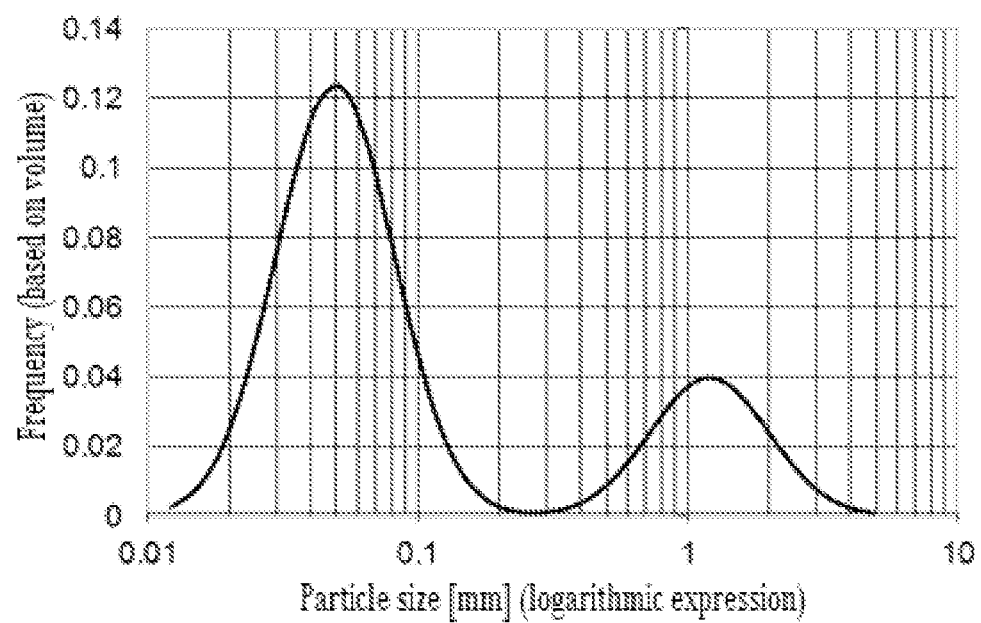

METHOD FOR PRODUCING CATALYST FOR AMMOXIDATION, AND METHOD FOR PRODUCING ACRYLONITRILE

TECHNICAL FIELD

The present invention relates to a method for producing a catalyst for ammoxidation for use in producing acrylonitrile by reacting propylene, molecular oxygen, and ammonia, and a method for producing acrylonitrile using the catalyst for ammoxidation produced by the method.

BACKGROUND ART

A method of producing acrylonitrile by reacting propylene, molecular oxygen, and ammonia is known as "ammoxidation reaction". This reaction is used worldwide as an industrial process of producing acrylonitrile.

In this reaction, a composite oxide catalyst is utilized for achieving a favorable acrylonitrile yield. For example, a catalyst containing Mo—Bi—Fe or Fe—Sb as an essential component is industrially used. Studies on improvement in metal composition have been continued in order to achieve a more favorable acrylonitrile yield (see, for example, Patent Documents 1 and 2).

Meanwhile, attempts have also been made to improve the yield of acrylonitrile not only by improvement in metal composition but by improvement in catalyst preparation step. For example, Patent Document 3 discloses a method for producing a catalyst for acrylonitrile production, comprising preparing a slurry containing molybdenum, bismuth, iron, tungsten, and the like at a temperature in the range of 30 to 70° C. Patent Document 4 discloses a method for producing a catalyst for acrylonitrile production, comprising keeping a slurry for a given time under particular conditions during a step.

Patent Document 5 discloses a method for producing a catalyst for acrylonitrile production, comprising adjusting the particle size of an aggregate contained in a precursor slurry of the catalyst by carrying out homogenizer treatment and ultrasonic treatment on the precursor slurry.

LIST OF PRIOR ART DOCUMENTS

Patent Document

Patent Document 1: Japanese Patent No. 5919870
Patent Document 2: Japanese Patent No. 4954750
Patent Document 3: Japanese Patent No. 4823950
Patent Document 4: Japanese Patent No. 4425743
Patent Document 5: Japanese Patent No. 5378041

SUMMARY OF INVENTION

Problems to be Solved by Invention

However, these catalyst production methods are still insufficient for improvement in the yield of acrylonitrile, though these methods are effective to some extent for the improvement. Thus, further improvement is demanded.

Patent Document 5 discloses a method of controlling the particle size of an aggregate in a slurry by pulverization using a homogenizer. In general, the pulverization using a homogenizer is called disruption, and a mechanism by which an aggregate is disintegrated into smaller aggregates has been proposed. However, primary particles constituting the aggregate are pulverized by physical impact, and particle surface is activated by the formation of new surface or lattice defect, etc. so that the interaction between the particles is increased. As a result, the slurry loses stability by the reaggregation of the pulverized primary particles. This might reduce catalyst performance.

The present invention has been made in light of the problems described above. An object of the present invention is to provide a method for producing a catalyst for ammoxidation that exhibits a high acrylonitrile yield, and a method for producing acrylonitrile.

Means for Solving Problems

The present inventors have conducted diligent studies to attain the object, and consequently completed the present invention by finding that the object can be attained by a method for producing a catalyst, comprising adjusting the particle sizes of metal primary particles constituting an aggregate containing a metal and a carrier in a precursor slurry to a particular range by optimizing conditions for precursor slurry preparation.

Specifically, the present invention is as follows.

[1]

A method for producing a catalyst for ammoxidation, comprising steps of:

preparing a catalyst precursor slurry comprising a liquid phase and a solid phase;

drying the catalyst precursor slurry to obtain a dry particle; and calcining the dry particle to obtain a catalyst for ammoxidation, wherein the solid phase of the catalyst precursor slurry comprises an aggregate containing a metal and a carrier, metal primary particles constituting the aggregate have a particle size of 1 μm or smaller, and an average particle size of the metal primary particles is 40 nm or larger and 200 nm or smaller.

[2]

The method for producing the catalyst for ammoxidation according to [1], wherein the catalyst for ammoxidation comprises a composite metal oxide having composition represented by the following general formula (1):

$$Mo_{12}Bi_aFe_bX_cY_dZ_eO_f \qquad (1)$$

wherein X represents one or more elements selected from the group consisting of nickel, cobalt, magnesium, calcium, zinc, strontium, and barium; Y represents one or more elements selected from the group consisting of cerium, chromium, lanthanum, neodymium, yttrium, praseodymium, samarium, aluminum, gallium, and indium; Z represents one or more elements selected from the group consisting of potassium, rubidium and cesium; a represents the atomic ratio of bismuth to the 12 atoms of molybdenum and satisfies $0.1 \leq a \leq 2.0$; b represents the atomic ratio of iron to the 12 atoms of molybdenum and satisfies $0.1 \leq b \leq 3.0$; c represents the atomic ratio of X to the 12 atoms of molybdenum and satisfies $0.1 \leq c \leq 10.0$; d represents the atomic ratio of Y to the 12 atoms of molybdenum and satisfies $0.1 \leq d \leq 3.0$; e represents the atomic ratio of Z to the 12 atoms of molybdenum and satisfies $0.01 \leq e \leq 2.0$; and f represents the atomic ratio of oxygen to the 12 atoms of molybdenum and is the number of atoms of oxygen necessary for satisfying valence requirements of other elements present.

[3]

The method for producing the catalyst for ammoxidation according to [1] or [2], wherein in the step of preparing the catalyst precursor slurry comprising the liquid phase and the solid phase, a free acid concentration in the slurry is 0.1% or more and 1.2% or less.

[4]
The method for producing the catalyst for ammoxidation according to any of [1] to [3], wherein in the step of preparing the catalyst precursor slurry comprising the liquid phase and the solid phase, the free acid concentration in the slurry is 0.8% or more and 1.2% or less.

[5]
The method for producing the catalyst for ammoxidation according to any of [1] to [4], wherein the catalyst for ammoxidation comprises a carrier, and a content of the carrier in the catalyst for ammoxidation is 35 to 45% by mass.

[6]
The method for producing the catalyst for ammoxidation according to any of [1] to [5], wherein in the step of preparing the catalyst precursor slurry comprising the liquid phase and the solid phase, a proportion of a total mass of the metal component and the carrier as starting materials to a mass of the whole catalyst precursor slurry is 10% by mass or more and 40% by mass or less.

[7]
The method for producing the catalyst for ammoxidation according to any of [1] to [6], wherein in the step of preparing the catalyst precursor slurry comprising the liquid phase and the solid phase, the proportion of the total mass of the metal component and the carrier as starting materials to the mass of the whole catalyst precursor slurry is 20% by mass or more and 35% by mass or less.

[8]
The method for producing the catalyst for ammoxidation according to any of [1] to [7], wherein in the step of drying the catalyst precursor slurry to obtain the dry particle, a dryer is kept at an inlet air temperature of 180 to 250° C. and at an outlet temperature of 100 to 150° C.

[9]
The method for producing the catalyst for ammoxidation according to any of [1] to [8], wherein the step of calcining the dry particles to obtain the catalyst for ammoxidation comprises denitration treatment before the calcination, and the denitration treatment involves performing heating at 150 to 450° C. for 1.5 to 3 hours.

[10]
The method for producing the catalyst for ammoxidation according to any of [1] to [9], wherein in the step of calcining the dry particles to obtain the catalyst for ammoxidation, a calcination temperature is 550 to 650° C.

[11]
A method for producing acrylonitrile, comprising steps of:
preparing a catalyst precursor slurry comprising a liquid phase and a solid phase;
drying the catalyst precursor slurry to obtain a dry particle;
calcining the dry particle to obtain a catalyst for ammoxidation; and
supplying the catalyst for ammoxidation to a fluidized reaction vessel in advance, and while circulating the catalyst in the fluidized reaction vessel, reacting propylene, molecular oxygen, and ammonia to obtain acrylonitrile,
wherein the solid phase of the catalyst precursor slurry comprises an aggregate containing a metal and a carrier, metal primary particles constituting the aggregate have a particle size of 1 μm or smaller, and an average particle size of the metal primary particles is 40 nm or larger and 200 nm or smaller.

[12]
The method for producing acrylonitrile according to [11], wherein
a source of the molecular oxygen is air, and
a molar ratio of ammonia and air to propylene is in the range of 1/(0.8 to 1.4)/(7 to 12) in terms of a ratio of propylene/ammonia/air.

[13]
The method for producing acrylonitrile according to [11], wherein
a source of the molecular oxygen is air, and
a molar ratio of ammonia and air to propylene is in the range of 1/(0.9 to 1.3)/(8 to 11) in terms of a ratio of propylene/ammonia/air.

[14]
The method for producing acrylonitrile according to any of [11] to [13], wherein a temperature at which propylene, molecular oxygen, and ammonia are reacted in the presence of the catalyst for ammoxidation is in the range of 350 to 550° C.

[15]
The method for producing acrylonitrile according to any of claims [11] to [13], wherein a temperature at which propylene, molecular oxygen, and ammonia are reacted in the presence of the catalyst for ammoxidation is in the range of 400 to 500° C.

[16]
The method for producing acrylonitrile according to any of [11] to [15], wherein the catalyst for ammoxidation comprises a composite metal oxide having composition represented by the following general formula (1):

$$Mo_{12}Bi_aFe_bX_cY_dZ_eO_f \qquad (1)$$

wherein X represents one or more elements selected from the group consisting of nickel, cobalt, magnesium, calcium, zinc, strontium, and barium; Y represents one or more elements selected from the group consisting of cerium, chromium, lanthanum, neodymium, yttrium, praseodymium, samarium, aluminum, gallium, and indium; Z represents one or more elements selected from the group consisting of potassium, rubidium and cesium; a represents the atomic ratio of bismuth to the 12 atoms of molybdenum and satisfies $0.1 \le a \le 2.0$; b represents the atomic ratio of iron to the 12 atoms of molybdenum and satisfies $0.1 \le b \le 3.0$; c represents the atomic ratio of X to the 12 atoms of molybdenum and satisfies $0.1 \le c \le 10.0$; d represents the atomic ratio of Y to the 12 atoms of molybdenum and satisfies $0.1 \le d \le 3.0$; e represents the atomic ratio of Z to the 12 atoms of molybdenum and satisfies $0.01 \le e \le 2.0$; and f represents the atomic ratio of oxygen to the 12 atoms of molybdenum and is the number of atoms of oxygen necessary for satisfying valence requirements of other elements present.

[17]
The method for producing acrylonitrile according to any of [11] to [16], wherein in the step of preparing the catalyst precursor slurry comprising the liquid phase and the solid phase, a free acid concentration in the slurry is 0.1% or more and 1.2% or less.

[18]
The method for producing acrylonitrile according to any of [11] to [17], wherein in the step of preparing the catalyst precursor slurry comprising the liquid phase and the solid phase, the free acid concentration in the slurry is 0.8% or more and 1.2% or less.

[19]
The method for producing acrylonitrile according to any of [11] to [18], wherein the catalyst for ammoxidation comprises a carrier, and a content of the carrier in the catalyst for ammoxidation is 35 to 45% by mass.

[20]
The method for producing acrylonitrile according to any of [11] to [19], wherein in the step of preparing the catalyst precursor slurry comprising the liquid phase and the solid phase, a proportion of the total mass of the metal component and the carrier as starting materials to the mass of the whole catalyst precursor slurry is 10% by mass or more and 40% by mass or less.

[21]
The method for producing acrylonitrile according to any of [11] to [20], wherein in the step of preparing the catalyst precursor slurry comprising the liquid phase and the solid phase, the proportion of the total mass of the metal component and the carrier as starting materials to the mass of the whole catalyst precursor slurry is 20% by mass or more and 35% by mass or less.

[22]
The method for producing acrylonitrile according to any of [11] to [21], wherein in the step of drying the catalyst precursor slurry to obtain dry particles, a dryer is kept at an inlet air temperature of 180 to 250° C. and at an outlet temperature of 100 to 150° C.

[23]
The method for producing acrylonitrile according to any of [11] to [22], wherein the step of calcining the dry particles to obtain a catalyst for ammoxidation comprises denitration treatment before the calcination, and the denitration treatment involves performing heating at 150 to 450° C. for 1.5 to 3 hours.

[24]
The method for producing acrylonitrile according to any of [11] to [23], wherein in the step of calcining the dry particles to obtain a catalyst for ammoxidation, a calcination temperature is 550 to 650° C.

Advantages of Invention

The present invention can provide a method for producing a catalyst for ammoxidation that exhibits a high acrylonitrile yield in the ammoxidation reaction of propylene, and a method for producing acrylonitrile with a high yield.

BRIEF DESCRIPTION OF DRAWING

The FIGURE is a conceptual diagram of one example of measurement results when an aggregate in a catalyst precursor slurry is measured by an ultrasonic attenuation method.

MODE FOR CARRYING OUT INVENTION

Hereinafter, the mode for carrying out the present invention (hereinafter, simply referred to as the "present embodiment") will be described. However, the present invention is not limited by the embodiment given below. Various changes or modifications can be made therein without departing from the spirit of the present invention.

The method for producing a catalyst for ammoxidation according to the present embodiment comprises steps of:
preparing a catalyst precursor slurry comprising a liquid phase and a solid phase;
drying the catalyst precursor slurry to obtain dry particles; and
calcining the dry particles to obtain a catalyst for ammoxidation,
wherein the solid phase of the catalyst precursor slurry comprises an aggregate containing a metal and a carrier, metal primary particles constituting the aggregate have a particle size of 1 μm or smaller, and an average particle size of the metal primary particles is 40 nm or larger and 200 nm or smaller.

In the method for producing the catalyst for ammoxidation according to the present embodiment, it is preferred to first prepare the catalyst precursor slurry comprising the liquid phase and the solid phase by mixing starting materials of components constituting the catalyst, such as a metal and a carrier. In the case of using, for example, silica, as the carrier, metal particles and silica which are insoluble in a solvent in the slurry accumulate in the catalyst precursor slurry to constitute an aggregate. The state of this aggregate can be observed by a method known in the art. The aggregation of metal primary particles and silica particles can be observed, for example, by extracting the aggregate onto a replica film by a freeze-fracture replica method, and carrying out scanning electron microscope (SEM) measurement. In this operation, energy dispersive X-ray (EDX) spectroscopy can be used in combination therewith to confirm that the particles constituting the aggregate are metal and silica.

In the present embodiment, the particle sizes of metal primary particles constituting the aggregate can be calculated by measuring the catalyst precursor slurry in an undiluted form using a particle size distribution meter based on an ultrasonic attenuation method which is a method known in the art. The ultrasonic attenuation method is an approach which involves generating ultrasonic wave from an ultrasonic generator, observing the ultrasonic wave that has traveled to a detector through a slurry in a sample cell, and determining a particle size distribution from results about the rate of attenuation of ultrasonic wave (ultrasonic attenuation spectrum) in the slurry. The ultrasonic attenuation method is characterized in that a highly concentrated slurry can be measured in an undiluted form without being diluted, and thus has the advantage that the influence of change in slurry state caused by dilution can be eliminated. Other measurement methods, such as a laser diffraction method or a dynamic light scattering method, which require diluting a slurry at the time of preparation of a measurement sample, might aggregate metal and/or silica particles by dilution and are not suitable for the measurement of the primary particle size of a metal. In the present embodiment, the measurement of the primary particle size of the metal is carried out using AcoustoSizer IIX from Kyowa Interface Science Co., Ltd. The FIGURE shows a conceptual diagram of one example of measurement results when the aggregate in the catalyst precursor slurry used in the present embodiment is measured by the ultrasonic attenuation method. As shown in the FIGURE, two peaks are observed on a graph with a particle size (logarithmic expression) on the abscissa against frequency based on volume on the ordinate. In light of the fact that the left peak of nm order in the FIGURE is dominant from the viewpoint of the number of particles, results of observing the aggregate in the slurry by the method mentioned above, and the fact that % by mass of the carrier (e.g., silica) in the aggregate is low as mentioned later, the left peak of nm order is defined as being derived from primary particles of the metal, and the right peak of μm order is defined as being derived from the aggregate itself containing the metal and the carrier (e.g., silica). In the present embodiment, the modal diameter of the left peak of nm order is regarded as an "average particle size of the metal primary particles". It is considered that the metal primary particles constituting the aggregate are oscillated by ultrasonic irradiation at the time of measurement so that the particle sizes of the metal primary particles can be measured. Detailed measurement and analysis conditions will be mentioned later. In the method for producing the catalyst for ammoxidation according to the present embodiment, the range of the average particle size of the metal primary particles constituting the aggregate containing the metal and the carrier (e.g., silica) in the catalyst precursor slurry is 40 nm as the lower limit and 200 nm as the upper limit. The average particle size of the metal primary particles is preferably 45 nm or larger and 180 nm or smaller, more preferably 45 nm or larger and 150 nm or smaller, further preferably 50 nm or larger and 130 nm or smaller. The particle sizes of the metal primary particles are adjusted to 1 μm or smaller. The lower limit of the particle sizes of the metal primary particles is not particularly limited and is, for example, 10 nm or larger. When the particle sizes of the metal primary particles fall within the range described above, the particle size distribution of the metal primary particles is not too wide and can prevent the structure of the aggregate from being distorted. Therefore, an acrylonitrile yield is improved.

When the average particle size of the metal primary particles is equal to or more than the lower limit, the point of decomposition of acrylonitrile is decreased in number with decrease in metal particle surface in the catalyst so that the secondary decomposition of the target acrylonitrile is suppressed. Hence, an acrylonitrile yield is improved.

When the average particle size of the metal primary particles is equal to or less than the upper limit, the point of reaction for acrylonitrile synthesis is increased in number with increase in metal particle surface. Hence, an acrylonitrile yield is improved. When average particle size of the metal primary particles is equal to or less than the upper limit, the aggregate containing the metal and the carrier (e.g., silica) is not too large and can be prevented from being precipitated in a slurry preparation vessel or a liquid feed line at the time of catalyst production.

On the other hand, the particle sizes of non-metal particles are not particularly limited. In the case of using, for example, a silica sol, as a starting material of a carrier, the average particle size of silica can be adjusted in consideration of the activity of the catalyst, etc.

Examples of the method for controlling the particle sizes of the metal primary particles constituting the aggregate in the catalyst precursor slurry include, but are not particularly limited to, the following method: for example, in the case of preparing the catalyst precursor slurry comprising the solid phase and the liquid phase by dispersing or dissolving starting materials to prepare solutions, and mixing a plurality of solutions to form an aggregate, examples thereof include a method of setting a free acid concentration in the catalyst precursor slurry, the mass ratio between the metal and the carrier, % by mass of the metal and the carrier based on the whole slurry at the time of catalyst precursor slurry preparation, stirring power at the time of mixing, or the mixing rate of starting material solutions to within a particular range, and the selection of an additive for catalyst precursor slurry preparation.

Particularly, the particle sizes of the metal primary particles can be set to a particular range by appropriately combining stirring power for a silica sol, a molybdenum solution, and an aqueous metal nitrate solution mentioned later with the addition time of the aqueous metal nitrate solution. The addition time of the aqueous metal nitrate solution is preferably, for example, 10 to 80 seconds.

In the case of using starting materials in a solid form, examples thereof include a method of controlling the particle sizes of the solid starting materials by pulverization.

The step of preparing the catalyst precursor slurry is not particularly limited by a preparation approach as long as the requirements related to the particle sizes of the metal primary particles constituting the aggregate in the catalyst precursor slurry described above are satisfied. A preparation method known in the art can be appropriately selected and used.

The composition of the catalyst for ammoxidation used in the present embodiment is not particularly limited and is preferably, as one example, composition containing molybdenum, bismuth, and iron represented by the general formula (1) given below. Molybdenum plays a role as an adsorption site for propylene and an active site for ammonia. Bismuth plays a role in activating propylene, extracting hydrogen at position α, and forming a π allyl species. Iron plays a role in supplying oxygen present in a vapor phase by trivalent/divalent redox to a catalytic active point. Such composition tends to further improve the rate of acrylonitrile selection.

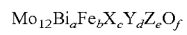  (1)

In the formula (1), X represents one or more elements selected from the group consisting of nickel, cobalt, magnesium, calcium, zinc, strontium, and barium, Y represents one or more elements selected from the group consisting of cerium, chromium, lanthanum, neodymium, yttrium, praseodymium, samarium, aluminum, gallium, and indium, and Z represents one or more elements selected from the group consisting of potassium, rubidium and cesium. a represents the atomic ratio of bismuth to the 12 atoms of molybdenum and satisfies 0.1≤a≤2.0, preferably 0.15≤a≤1.0, more preferably 0.2≤a≤0.7. b represents the atomic ratio of iron to the 12 atoms of molybdenum and satisfies 0.1≤b≤3.0, preferably 0.5≤b≤2.5, more preferably 1.0≤b≤2.0. c represents the atomic ratio of X to the 12 atoms of molybdenum and satisfies 0.1≤c≤10.0, preferably 3.0≤c≤9.0, more preferably 5.0≤c≤8.5. d represents the atomic ratio of Y to the 12 atoms of molybdenum and satisfies 0.1≤d≤3.0, preferably 0.2≤d≤2.0, more preferably 0.3 d≤1.5. e represents the atomic ratio of Z to the 12 atoms of molybdenum and satisfies 0.01≤e≤2.0, preferably 0.05≤e≤1.0. f represents the atomic ratio of oxygen to the 12 atoms of molybdenum and is the number of atoms of oxygen necessary for satisfying valence requirements of other elements present.

The method for producing the catalyst for ammoxidation according to the present embodiment comprises the steps of: (1) preparing a precursor slurry (catalyst precursor slurry) comprising a liquid phase and a solid phase and serving as a precursor of the catalyst; (2) drying the catalyst precursor slurry to obtain dry particles; and (3) calcining the dry particles to obtain the catalyst for ammoxidation.

The step (1) is the step of preparing the precursor slurry comprising the liquid phase and the solid phase and serving as a precursor of the catalyst, for example, by mixing each element with a carrier. Examples of the element source of each element include ammonium salts, nitrate, and organic acid salts soluble in water or an acidic aqueous solution. These sources are preferred because the sources cause neither residual chloride from hydrochloride used nor residual sulfur from sulfate used.

The starting material of the carrier is not particularly limited as long as the starting material is one usually used. Examples thereof include oxides such as silica, alumina, titania, and zirconia. Among them, silica is preferred. Silica compared with other oxides is inactive in itself and has a favorable binding effect on active catalyst components.

The order of mixing components in preparing the catalyst precursor slurry is not particularly limited. For example, an exemplary embodiment of the composition represented by the general formula (1) is as described below. First, an ammonium salt of molybdenum dissolved in warm water (hereinafter, referred to as a molybdenum solution) is added to a silica sol (hereinafter, referred to as a silica solution). Next, a solution containing nitrate as an element source of each element such as bismuth, cerium, iron, chromium, nickel, magnesium, zinc, manganese, cobalt, rubidium, cesium, or potassium dissolved in an aqueous nitric acid solution (hereinafter, referred to as an aqueous metal nitrate solution) is added thereto to obtain a catalyst precursor slurry. Alternatively, the catalyst precursor slurry is not necessarily required to contain all the elements constituting the catalyst, and the starting material of an element that is not contained in the catalyst precursor slurry may be added in each step before the drying step or may be added by a method such as impregnation to the catalyst after drying.

In the method for preparing the starting material slurry mentioned above, the pH of the slurry can be changed by adjusting the concentration of nitric acid used or adding ammonia water to the silica sol, the molybdenum solution, or the aqueous metal nitrate solution. Also, the precursor slurry can be prepared by appropriately adding a water-soluble polymer such as polyethylene glycol, methylcellulose, polyvinyl alcohol, polyacrylic acid, or polyacrylamide, amines, carboxylic acids, aminocarboxylic acids, or other organic acids to the silica sol, the molybdenum solution, or the aqueous metal nitrate solution. Among these additives, imidazole or carboxylic acid is preferred, nitrilotriacetic acid or oxalic acid is more preferred, and oxalic acid is further preferred. Primary or secondary amines having NH might generate a gel of the molybdenum solution. In the case of using these amines as additives, the metal primary particle sizes in the catalyst precursor slurry tend to be increased. It is also preferred to mix a silica starting material and an oxalic acid starting material in advance.

The content of carboxylic acid in the catalyst precursor slurry is preferably 0.01 to 0.10 molar equivalents based on the sum of the metal elements constituting the catalyst for ammoxidation. The content is more preferably 0.02 to 0.07 molar equivalents. When the content of carboxylic acid is 0.01 molar equivalents or more, the resulting catalyst tends to further improve an acrylonitrile yield. When the content of carboxylic acid is 0.10 molar equivalents or less, heat generation ascribable to the decomposition of carboxylic acid and cracks in catalyst particles are suppressed at the stage of catalyst production. Thus, the strength of the resulting catalyst tends to be further improved.

Hereinafter, the method for controlling the particle sizes of the metal primary particles constituting the aggregate in the catalyst precursor slurry mentioned above will be described in detail.

The free acid concentration is the following parameter.

Free acid concentration (%)=Molecular weight of an acid×(The number of moles of the acid used−The number of moles of the base used)/Mass of the whole catalyst precursor slurry×100

In this context, the acid refers to a strong acid and does not correspond to a weak acid such as carboxylic acid. When the free acid concentration is high, the amount of a metal dissolved in the liquid phase of the catalyst precursor slurry is increased. Therefore, the metal primary particle sizes in the aggregate in the slurry are decreased. On the other hand, when the free acid concentration is low, the amount of a metal precipitated is increased. Therefore, the metal primary particle sizes in the aggregate in the catalyst precursor slurry are increased. The free acid concentration is preferably 0.1% or more and 1.2% or less, more preferably 0.8% or more and 1.2% or less.

When a volatile acid and base are used, the free acid concentration might be changed due to the volatilization of these components at the time of heating and stirring during the preparation of the catalyst precursor slurry. Hence, it is preferred to carry out the preparation of the starting material solution or the stirring of the catalyst precursor slurry in a closed container.

The mass ratio between a metal oxide and the carrier in the catalyst for ammoxidation is preferably metal oxide: carrier=55:45 to 65:35. In the case of increasing the content of the carrier, the primary particle size of the metal tends to be decreased, though the reason for this is not clear. The content of the carrier is preferably 35% by mass or more from the viewpoint of strength such as fracture resistance or abrasion resistance under practical conditions.

The proportion of the total mass of the metal component and the carrier as starting materials to the mass of the whole catalyst precursor slurry is preferably 10% by mass or more and 40% by mass or less, more preferably 20% by mass or more and 35% by mass or less. When % by mass of the metal and the carrier based on the whole catalyst precursor slurry is equal to or more than the lower limit, the absolute amount of the metal in the catalyst precursor slurry is increased while the amount of a metal dissolved in the liquid phase is decreased. Therefore, the particle sizes of the metal primary particles constituting the aggregate are increased. When % by mass of the metal and the carrier based on the whole catalyst precursor slurry is equal to or less than the upper limit, the viscosity of the catalyst precursor slurry is decreased so that the catalyst precursor slurry has favorable fluidity. Thus, poor shaping of a catalyst powder can be suppressed at the time of spray drying.

The stirring power at the time of solution mixing is preferably 50 rpm or more and 400 rpm or less. When the stirring power is equal to or more than the lower limit, the solutions are sufficiently mixed so that the primary particle size of the metal is decreased. When the stirring power is equal to or less than the upper limit, air bubbles are prevented from being taken in during slurry stirring. Thus, poor shaping of a catalyst powder can be suppressed at the time of spray drying.

It is preferred to gradually elevate the stirring power at the time of solution mixing. It is preferred to gradually elevate the stirring power so as to be in the range of 120 rpm or more and 300 rpm or less at stage (2) of adding an aqueous molybdenum solution to an aqueous silica solution and in the range of 150 rpm or more and 400 rpm or less at stage (3) of adding an aqueous metal nitrate solution to the aqueous silica-molybdenum solution. The stirring power is more preferably in the range of 150 rpm or more and 250 rpm or less at the stage (2) and in the range of 150 rpm or more and 300 rpm or less at the stage (3), further preferably in the range of 180 rpm or more and 200 rpm or less at the stage (2) and in the range of 200 rpm or more and 300 rpm or less at the stage (3).

When the starting material solutions are mixed (e.g., in the exemplary embodiment mentioned above, when the silica solution and the molybdenum solution are mixed, or when the mixed solution of silica and molybdenum and the aqueous nitrate solution are mixed), it is preferred to complete the mixing of a newly added solution in 15 seconds or longer and 3 minutes or shorter. When the mixing time is equal to or more than the lower limit, the solutions are uniformly mixed so that the performance of the resulting catalyst is improved. When the mixing time is equal to or less than the upper limit, the particle sizes of the metal primary particles constituting the aggregate are decreased, though the reason for this is not clear.

In the present embodiment, the particle sizes of the metal primary particles constituting the aggregate are measured using AcoustoSizer IIX from Kyowa Interface Science Co., Ltd. The measurement is carried out using the catalyst precursor slurry in an undiluted form and the slurry liquid phase. A filtrate obtained by filtering the catalyst precursor slurry through a filter having an opening of 1 µm is defined as a liquid phase, and a filtrate residue that has not passed through the filter is defined as a solid phase. When scanning electron microscope (SEM) measurement was actually carried on a replica film of the liquid phase prepared by the freeze-fracture replica method mentioned above, neither the aggregate contained in the catalyst precursor slurry in an undiluted form nor the metal primary particles constituting the aggregate were observed in the liquid phase. The slurry aggregate becomes caky and remains as a residue on the filter paper during filtration. In short, the solid phase can be defined as a cluster of aggregates in the catalyst precursor slurry. In this context, liquid matter contained in the filtrate residue immediately after filtration is regarded as a liquid phase (attached liquid phase) and determined from decrease in mass after vacuum drying of the filtrate residue at 60° C. for 18 hours. In this respect, the composition of the attached liquid phase is the same as the composition of the filtrate. The mass of the solid phase is a mass after drying of the filtrate residue mentioned above, and the mass of the liquid phase is the total mass of the filtrate and the attached liquid phase. The ultrasonic attenuation spectrum of the liquid phase alone is subtracted from the ultrasonic attenuation spectrum of the catalyst precursor slurry to obtain an ultrasonic attenuation spectrum derived from the aggregate in the catalyst precursor slurry. The obtained ultrasonic attenuation spectrum of the solid phase can be analyzed with companion software using % by mass of the aggregate in the catalyst precursor slurry, the true density of the aggregate, and the permittivity of the aggregate to calculate particle sizes. % by mass of the aggregate in the catalyst precursor slurry is calculated by dividing the mass after drying of the solid phase by the mass of the whole catalyst precursor slurry. The true density and the permittivity of the aggregate are measured using a powder obtained by milling the dried solid phase by a method known in the art.

In Examples and Comparative Examples mentioned later, the modal diameter of the left peak of nm order shown in the FIGURE in analysis results obtained by the method described above was defined as an average particle size of the metal primary particles. This is based on the fact that the left peak of nm order in the FIGURE is dominant from the viewpoint of the number of particles, results of observing the aggregate in the slurry by the method mentioned above, and the fact that % by mass of the carrier (e.g., silica) based on the total mass of aggregates formed by a catalyst precursor slurry preparation method in Examples or Comparative Examples is small (3% by mass or less). % by mass of the carrier in the aggregate was calculated by completely dissolving a dried product of the solid phase in a mixed aqueous solution containing 5 parts of 36% by mass of hydrochloric acid, 10 parts of 57% by mass of hydroiodic acid and 2.5 parts of 47% by mass of hydrofluoric acid, and subsequently quantifying the amount of silicon using an ICP emission spectrophotometer.

The step (2) is the step of drying the catalyst precursor slurry to obtain dry particles. The step is preferably the step of spray-drying the catalyst precursor slurry to obtain dry particles. Spherical fine particles suitable for fluidized-bed reaction can be obtained by spray-drying the catalyst precursor slurry. A general apparatus such as rotary disc type or nozzle type can be used as a spray drying apparatus. The particle size of the resulting catalyst for ammoxidation can be adjusted by adjusting spray drying conditions. For use as a fluidized-bed catalyst, the particle size of the catalyst for ammoxidation is preferably 25 to 180 µm. One example of the conditions for obtaining the catalyst particles for ammoxidation having a preferred particle size includes spray drying that is performed by using a centrifugal spraying apparatus equipped with a dish-shaped rotator installed at the center of the upper part of a dryer, and keeping the dryer at an inlet air temperature of 180 to 250° C. and at an outlet temperature of 100 to 150° C.

The step (3) is the step of calcining the dry particles obtained by the drying to obtain a catalyst for ammoxidation. Since the dry particles may contain nitric acid, it is preferred to perform denitration treatment before the calcination. The denitration treatment preferably involves performing heating at 150 to 450° C. for 1.5 to 3 hours. The calcination can be performed in an air atmosphere. The calcination temperature is preferably 550 to 650° C. When the calcination temperature is 550° C. or higher, crystal growth proceeds sufficiently so that the acrylonitrile selectivity of the resulting catalyst tends to be further improved. When the calcination temperature is 650° C. or lower, the surface area of the resulting catalyst for ammoxidation is increased so that the reaction activity of propylene tends to be further improved. The gas atmosphere for use in the denitration and the calcination may be an oxidized gas atmosphere containing oxygen or may be an inert gas atmosphere, for example, nitrogen. Air is conveniently used.

The method for producing acrylonitrile according to the present embodiment comprises a reaction step of reacting propylene, molecular oxygen, and ammonia (ammoxidation reaction) in the presence of the catalyst for ammoxidation obtained by the method mentioned above to produce acrylonitrile. The production of acrylonitrile through the ammoxidation reaction can be carried out using a fixed-bed reactor or a fluidized-bed reactor (fluidized reaction vessel). Among them, a fluidized-bed reactor (fluidized reaction vessel) is preferred from the viewpoint of efficiently removing heat generated during the reaction, and enhancing the yield of acrylonitrile. In the case of performing the reaction step in a fluidized reaction vessel, it is preferred to supply the catalyst for ammoxidation to the fluidized reaction vessel in advance, and while circulating the catalyst in the fluidized reaction vessel, perform ammoxidation reaction. The starting materials propylene and ammonia for the ammoxidation reaction are not necessarily required to be highly pure, and industrial grade can be used. When the source of the molecular oxygen is air, the molar ratio among propylene, ammonia, and air (propylene/ammonia/air) in a starting material gas is preferably in the range of 1/(0.8 to 1.4)/(7 to 12), more preferably in the range of 1/(0.9 to 1.3)/(8 to 11). The reaction temperature is in the range of preferably 350 to 550° C., more preferably 400 to 500° C. The reaction pressure is preferably normal pressure to 0.3 MPa. The contact time of the starting material gas with the catalyst for ammoxidation is preferably 2 to 7 seconds, more preferably 3 to 6 seconds.

The reaction tube for use in the ammoxidation reaction of propylene is not particularly limited. For example, a Pyrex® glass tube having an inside diameter of 25 mm and containing sixteen 10-mesh wire sheets at 1-cm intervals can be used. A specific example of the ammoxidation reaction is not particularly limited. For example, first, the amount of the catalyst for ammoxidation is set to 50 cc, the reaction temperature is set to 430° C., and the reaction pressure is set to 0.17 MPa. A mixed gas (propylene, ammonia, oxygen, and helium) having a propylene volume of 9% is allowed to pass therethrough. Then, the volume ratio of ammonia to propylene is set such that a sulfuric acid consumption unit defined according to the expression given below is 20 kg/T-AN. In this respect, the ammonia/propylene molar ratio is defined as N/C. The volume ratio of oxygen to propylene is set such that the oxygen concentration of a gas at the reactor outlet is 0.2±0.02% by volume. In this respect, the molar quantity of oxygen is converted to the molar quantity of air provided that air contains 21% oxygen. In this respect, the air/propylene molar ratio is defined as A/C. The contact time defined according to the expression given below can be changed by changing the flow rate of the mixed gas. The rate of conversion of propylene defined according to the expression given below can thereby be set to 99.3±0.2%. The sulfuric acid consumption unit, the contact time, the rate of conversion of propylene, and the acrylonitrile yield are defined according to the following expressions.

$$\text{Sulfuric acid comsumption unit (kg/}T\text{-}AN) = \frac{\text{Weight of sulfuric acid necessary for neutralizing unreacted ammonia (kg)}}{\text{(Weight of produced acrylonitrile }(T))}$$

$$\text{Contact time (sec)} = \frac{\text{Amount of catalyst (cc)}}{\text{Flow rate of mixed gas(cc-}NTP\text{/sec)}} \times \frac{273}{273 + \text{Reaction Temperature}(°\text{ C.})} \times \frac{\text{Reaction pressure (MPa)}}{0.10}$$

$$\text{Rate of conversion of propylene(\%)} = \frac{\text{Consumed propylene (mol)}}{\text{Supplied propylene (mol)}} \times 100$$

$$\text{Acrylonitrile yield (\%)} = \frac{\text{Formed acrylonitrile (mol)}}{\text{Supplied propylene (mol)}} \times 100$$

EXAMPLES

Hereinafter, the present embodiment will be described in more detail with reference to Examples. However, the present embodiment is not limited by Examples given below. The catalyst composition described in Examples and Comparative Examples has the same value as the composition of each added element.

[Metal primary particle size]

In catalyst precursor slurries prepared in Examples and Comparative Examples, the particle sizes of the metal primary particles constituting the aggregate were measured as follows using AcoustoSizer IIX from Kyowa Interface Science Co., Ltd. The measurement was carried out using the catalyst precursor slurry in an undiluted form and the slurry liquid phase. A filtrate obtained by filtering the catalyst precursor slurry through a filter having an opening of 1 µm was defined as a liquid phase, and a filtrate residue that has not passed through the filter was defined as a solid phase. In short, the solid phase was defined as a cluster of aggregates in the catalyst precursor slurry. In this context, liquid matter contained in the filtrate residue immediately after filtration was regarded as a liquid phase (attached liquid phase) and determined from decrease in mass after vacuum drying of the filtrate residue at 60° C. for 18 hours. In this respect, the composition of the attached liquid phase was the same as the composition of the filtrate. The mass of the solid phase was a mass after drying of the filtrate residue mentioned above, and the mass of the liquid phase was the total mass of the filtrate and the attached liquid phase. The ultrasonic attenuation spectrum of the liquid phase alone was subtracted from the ultrasonic attenuation spectrum of the catalyst precursor slurry to obtain an ultrasonic attenuation spectrum derived from the aggregate in the catalyst precursor slurry. The obtained ultrasonic attenuation spectrum of the solid phase was analyzed with companion software using % by mass of the aggregate in the catalyst precursor slurry, the true density of the aggregate, and the permittivity of the aggregate to calculate particle sizes. % by mass of the aggregate in the catalyst precursor slurry was calculated by dividing the mass after drying of the solid phase by the mass of the whole catalyst precursor slurry. The true density of the aggregate was measured using a Wadon-type specific gravity bottle and a powder obtained by milling the dried solid phase. The permittivity of the aggregate was determined by adding a powder obtained by milling the dried solid phase into various solvents, followed by measurement using a permittivity measurement apparatus. In this respect, the permittivities of the solvent containing the powder obtained by milling the dried solid phase, and the solvent alone were measured, and a solvent was selected without difference therebetween. The permittivity of the solvent was hypothesized as the permittivity of the dried product of the solid phase.

The FIGURE shows a conceptual diagram of one example of measurement results when the aggregate in the catalyst precursor slurry is measured by the ultrasonic attenuation method. The modal diameter of the left peak of nm order shown in the FIGURE in analysis results obtained by the method described above was defined as an "average particle size of the metal primary particles". This is based on the fact that the left peak of nm order in the FIGURE is dominant from the viewpoint of the number of particles, results of observing the aggregate in the slurry by the method mentioned above, and the fact that % by mass of the carrier (e.g., silica) based on the total mass of aggregates formed by a catalyst precursor slurry preparation method in Examples or Comparative Examples is small (3% by mass or less). % by mass of the carrier in the aggregate was calculated by completely dissolving a dried product of the solid phase in a mixed aqueous solution containing 5 parts of 36% by mass of hydrochloric acid, 10 parts of 57% by mass of hydroiodic acid and 2.5 parts of 47% by mass of hydrofluoric acid, and subsequently quantifying the amount of silicon using an ICP emission spectrophotometer.

[Sulfuric acid consumption unit, contact time, rate of conversion of propylene, and acrylonitrile yield]

The reaction tube for use in the ammoxidation reaction of propylene was a Pyrex® glass tube having an inside diameter of 25 mm and containing sixteen 10-mesh wire sheets at 1-cm intervals. In ammoxidation reaction, the amount of the catalyst for ammoxidation was set to 50 cc, the reaction temperature was set to 430° C., and the reaction pressure was set to 0.17 MPa. A mixed gas (propylene, ammonia, oxygen, and helium) having a propylene volume of 9% was allowed to pass therethrough. Then, the volume ratio of ammonia to propylene was set such that a sulfuric acid consumption unit defined according to the expression given below was 20 kg/T-AN. In this respect, the ammonia/propylene molar ratio was defined as N/C. The volume ratio of oxygen to propylene was set such that the oxygen concentration of a gas at the reactor outlet was 0.2±0.02% by volume. In this respect, the molar quantity of oxygen was converted to the molar quantity of air provided that air contained 21% oxygen. In this respect, the air/propylene molar ratio was defined as A/C. The contact time defined according to the expression given below was changed by changing the flow rate of the mixed gas. The rate of conversion of propylene defined according to the expression given below was thereby set to 99.3±0.2%. The sulfuric acid consumption unit, the contact time, the rate of conversion of propylene, and the acrylonitrile yield were defined according to the following expressions.

Sulfuric acid comsumption unit (kg/$T$-$AN$) =

$$\frac{\text{Weight of sulfuric acid necessary for neutralizing unreacted ammonia (kg)}}{(\text{Weight of produced acrylonitrile}(T))}$$

Contact time (sec) = $\frac{\text{Amount of catalyst (cc)}}{\text{Flow rate of mixed gas(cc-}NTP\text{/sec)}} \times$ $$\frac{273}{273 + \text{Reaction temperature}(° \text{C.})} \times \frac{\text{Reaction pressure (MPa)}}{0.10}$$

Rate of conversion of propylene(%) =

$$\frac{\text{Consumed propylene (mol)}}{\text{Supplied propylene (mol)}} \times 100$$

Acrylonitrile yield (%) = $\frac{\text{Formed acrylonitrile (mol)}}{\text{Supplied propylene (mol)}} \times 100$

Example 1

A catalyst in which a metal oxide having metal component composition represented by $Mo_{12.00}Bi_{0.47}Ce_{0.99}Fe_{1.88}Ni_{3.08}Co_{3.90}Rb_{0.15}$ was supported on silica (metal oxide: 60% by mass, silica: 40% by mass) was produced by the following procedures.

First, 1333 g of a silica sol containing 30% by mass of $SiO_2$ was placed in a container with a lid and kept at 40° C., and 25.0 g of oxalic acid dihydrate dissolved in 287.5 g of water was added thereto with stirring at a stirring rotation speed of 120 rpm. After closing of the lid, the mixture was stirred for 10 minutes to prepare an aqueous silica solution. In another container with a lid, 476.7 g of ammonium paramolybdate [$(NH_4)_6Mo_7O_{24} \cdot 4H_2O$] was placed and dissolved in 850.8 g of warm water of 60° C. After cooling to 45° C., 35.8 g of 15% by mass of an aqueous ammonia solution was added thereto to prepare an aqueous molybdenum solution. In a further alternative container with a lid, 51.6 g of bismuth nitrate [$Bi(NO_3)_3 \cdot 5H_2O$], 96.1 g of cerium nitrate [$Ce(NO_3)_3 \cdot 6H_2O$], 171.2 g of iron nitrate [$Fe(NO_3)_3 \cdot 9H_2O$], 203.4 g of nickel nitrate [$Ni(NO_3)_2 \cdot 6H_2O$], 258.8 g of cobalt nitrate [$Co(NO_3)_2 \cdot 6H_2O$], and 5.0 g of rubidium nitrate [$RbNO_3$] were dissolved in 393.3 g of 16.6% by mass of nitric acid and kept at 40° C. to prepare an aqueous nitrate solution. The aqueous molybdenum solution was added in 1 minute to the aqueous silica solution kept at 40° C. with stirring at a stirring rotation speed of 200 rpm to obtain an aqueous silica-molybdenum solution. The obtained solution was stirred for 5 minutes and then continuously kept at 40° C., and the aqueous nitrate solution was added in 1 minute to the aqueous silica-molybdenum solution with stirring at a stirring rotation speed of 250 rpm to prepare a starting material slurry. The starting material slurry was stirred at 40° C. for 45 minutes while covered with the lid to prepare a catalyst precursor slurry comprising a liquid phase and a solid phase. The aggregation of metal primary particles and silica particles was able to be observed by extracting aggregates in the catalyst precursor slurry onto a replica film by the freeze-fracture replica method, and carrying out SEM measurement. In this operation, EDX measurement was able to be used in combination therewith to confirm that the particles constituting the aggregates were metal and silica. The obtained catalyst precursor slurry was used in measurement as described above to reveal that % by mass of the aggregates in the catalyst precursor slurry was 16.1% by mass, the true density of the aggregates was 2.7 g/mL, and the permittivity of the aggregate was 6. The attenuation spectrum of the catalyst precursor slurry measured by the ultrasonic attenuation method using Acousto-Sizer IIX from Kyowa Interface Science Co., Ltd. was analyzed using these parameters. As a result, the average particle size of the metal primary particles constituting the aggregates was calculated as 61 nm. The range of the particle sizes of the metal primary particles was 1 μm or smaller.

The obtained catalyst precursor slurry was dried using a rotary disc-type spray dryer to obtain dry particles. In this operation, the air temperature at the dryer inlet was set to 230° C., and the air temperature at the outlet was set to 110° C. The rotation speed of the disc was set to 12500 rpm. The obtained dry particles were kept at 200° C. for 5 minutes, heated at 2.5° C./min from 200° C. to 450° C., and kept at 450° C. for 20 minutes for denitration. The denitrated dry particles were calcined at 595° C. for 2 hours to obtain a catalyst for ammoxidation. The obtained catalyst for ammoxidation was supplied to a fluidized reaction vessel in advance. While the catalyst was circulated in the fluidized reaction vessel, propylene, molecular oxygen, and ammonia were reacted (ammoxidation reaction) to produce acrylonitrile. An ammonia/propylene molar ratio (N/C), an air/propylene molar ratio (A/C), and an acrylonitrile yield were determined. The results are shown in Table 1.

Example 2

A catalyst in which a metal oxide having metal component composition represented by $Mo_{12.00}Bi_{0.47}Ce_{0.99}Fe_{1.88}Ni_{3.08}Co_{3.90}Rb_{0.15}$ was supported on silica (metal oxide: 60% by mass, silica: 40% by mass) was produced by the following procedures.

First, 1333 g of a silica sol containing 30% by mass of $SiO_2$ was placed in a container with a lid and kept at 40° C., and 25.0 g of oxalic acid dihydrate dissolved in 287.5 g of water was added thereto with stirring at a stirring rotation speed of 120 rpm. After closing of the lid, the mixture was stirred for 10 minutes to prepare an aqueous silica solution. In another container with a lid, 476.7 g of ammonium paramolybdate [$(NH_4)_6Mo_2O_{24} \cdot 4H_2O$] was placed and dissolved in 850.8 g of warm water of 60° C. After cooling to 45° C., 35.8 g of 15% by mass of an aqueous ammonia solution was added thereto to prepare an aqueous molybdenum solution. In a further alternative container with a lid, 51.6 g of bismuth nitrate [$Bi(NO_3)_3 \cdot 5H_2O$], 96.1 g of cerium nitrate [$Ce(NO_3)_3 \cdot 6H_2O$], 171.2 g of iron nitrate [Fe (NO$_3$)$_3$.9H$_2$O], 203.4 g of nickel nitrate [Ni(NO$_3$)$_2$.6H$_2$O], 258.8 g of cobalt nitrate [Co(NO$_3$)$_2$.6H$_2$O], and 5.0 g of rubidium nitrate [RbNO$_3$] were dissolved in 393.3 g of 16.6% by mass of nitric acid and kept at 40° C. to prepare an aqueous nitrate solution. The aqueous molybdenum solution was added in 1 minute to the aqueous silica solution kept at 40° C. with stirring at a stirring rotation speed of 200 rpm to obtain an aqueous silica-molybdenum solution. The obtained solution was stirred for 5 minutes and then continuously kept at 40° C., and the aqueous nitrate solution was added in 1 minute to the aqueous silica-molybdenum solution with stirring at a stirring rotation speed of 275 rpm to prepare a starting material slurry. The starting material slurry was stirred at 40° C. for 45 minutes while covered with the lid to prepare a catalyst precursor slurry comprising a liquid phase and a solid phase. The aggregation of metal primary particles and silica particles was able to be observed by extracting aggregates in the catalyst precursor slurry onto a replica film by the freeze-fracture replica method, and carrying out SEM measurement. In this operation, EDX measurement was able to be used in combination therewith to confirm that the particles constituting the aggregates were metal and silica. The obtained catalyst precursor slurry was used in measurement as described above to reveal that % by mass of the aggregates in the catalyst precursor slurry was 16.1% by mass, the true density of the aggregates was 2.7 g/mL, and the permittivity of the aggregate was 6. The attenuation spectrum of the catalyst precursor slurry measured by the ultrasonic attenuation method using Acousto-Sizer IIX from Kyowa Interface Science Co., Ltd. was analyzed using these parameters. As a result, the average particle size of the metal primary particles constituting the aggregates was calculated as 57 nm. The range of the particle sizes of the metal primary particles was 1 μm or smaller.

The obtained catalyst precursor slurry was dried using a rotary disc-type spray dryer to obtain dry particles. In this operation, the air temperature at the dryer inlet was set to 230° C., and the air temperature at the outlet was set to 110° C. The rotation speed of the disc was set to 12500 rpm. The obtained dry particles were set at 200° C. for 5 minutes, heated at 2.5° C./min from 200° C. to 450° C., and kept at 450° C. for 20 minutes for denitration. The denitrated dry particles were calcined at 595° C. for 2 hours to obtain a catalyst for ammoxidation. The obtained catalyst for ammoxidation was supplied to a fluidized reaction vessel in advance. While the catalyst was circulated in the fluidized reaction vessel, propylene, molecular oxygen, and ammonia were reacted (ammoxidation reaction) to produce acrylonitrile. An ammonia/propylene molar ratio (N/C), an air/propylene molar ratio (A/C), and an acrylonitrile yield were determined. The results are shown in Table 1.

Example 3

A catalyst in which a metal oxide having metal component composition represented by Mo$_{12.00}$Bi$_{0.47}$Ce$_{0.99}$Fe$_{1.88}$Ni$_{3.08}$Co$_{3.90}$Rb$_{0.15}$ was supported on silica (metal oxide: 60% by mass, silica: 40% by mass) was produced by the following procedures.

First, 1333 g of a silica sol containing 30% by mass of SiO$_2$ was placed in a container with a lid and kept at 40° C. to prepare an aqueous silica solution. In another container with a lid, 476.7 g of ammonium paramolybdate [(NH$_4$)$_6$Mo$_7$O$_{24}$.4H$_2$O] was placed and dissolved in 850.8 g of warm water of 60° C. After cooling to 45° C., 35.8 g of 15% by mass of an aqueous ammonia solution was added thereto to prepare an aqueous molybdenum solution. In a further alternative container with a lid, 51.6 g of bismuth nitrate [Bi(NO$_3$)$_3$.5H$_2$O], 96.1 g of cerium nitrate [Ce(NO$_3$)$_3$.6H$_2$O], 171.2 g of iron nitrate [Fe(NO$_3$)$_3$.9H$_2$O], 203.4 g of nickel nitrate [Ni(NO$_3$)$_2$.6H$_2$O], 258.8 g of cobalt nitrate [Co(NO$_3$)$_2$.6H$_2$O], and 5.0 g of rubidium nitrate [RbNO$_3$] were dissolved in 393.3 g of 16.6% by mass of nitric acid and kept at 40° C. to prepare an aqueous nitrate solution. The aqueous molybdenum solution was added in 1 minute to the aqueous silica solution kept at 40° C. with stirring at a stirring rotation speed of 200 rpm to obtain an aqueous silica-molybdenum solution. The obtained solution was stirred for 5 minutes and then continuously kept at 40° C., and the aqueous nitrate solution was added in 1 minute to the aqueous silica-molybdenum solution with stirring at a stirring rotation speed of 250 rpm to prepare a starting material slurry. The starting material slurry was stirred at 40° C. for 45 minutes while covered with the lid to prepare a catalyst precursor slurry comprising a liquid phase and a solid phase. The aggregation of metal primary particles and silica particles was able to be observed by extracting aggregates in the catalyst precursor slurry onto a replica film by the freeze-fracture replica method, and carrying out SEM measurement. In this operation, EDX measurement was able to be used in combination therewith to confirm that the particles constituting the aggregates were metal and silica. The obtained catalyst precursor slurry was used in measurement as described above to reveal that % by mass of the aggregates in the catalyst precursor slurry was 16.1% by mass, the true density of the aggregates was 2.7 g/mL, and the permittivity of the aggregate was 6. The attenuation spectrum of the catalyst precursor slurry measured by the ultrasonic attenuation method using AcoustoSizer IIX from Kyowa Interface Science Co., Ltd. was analyzed using these parameters. As a result, the average particle size of the metal primary particles constituting the aggregates was calculated as 64 nm. The range of the particle sizes of the metal primary particles was 1 μm or smaller.

The obtained catalyst precursor slurry was dried using a rotary disc-type spray dryer to obtain dry particles. In this operation, the air temperature at the dryer inlet was set to 230° C., and the air temperature at the outlet was set to 110° C. The rotation speed of the disc was set to 12500 rpm. The obtained dry particles were kept at 200° C. for 5 minutes, heated at 2.5° C./min from 200° C. to 450° C., and kept at 450° C. for 20 minutes for denitration. The denitrated dry particles were calcined at 595° C. for 2 hours to obtain a catalyst for ammoxidation. The obtained catalyst for ammoxidation was supplied to a fluidized reaction vessel in advance. While the catalyst was circulated in the fluidized reaction vessel, propylene, molecular oxygen, and ammonia were reacted (ammoxidation reaction) to produce acrylonitrile. An ammonia/propylene molar ratio (N/C), an air/propylene molar ratio (A/C), and an acrylonitrile yield were determined. The results are shown in Table 1.

Example 4

A catalyst in which a metal oxide having metal component composition represented by Mo$_{12.00}$Bi$_{0.47}$Ce$_{0.99}$Fe$_{1.88}$Ni$_{3.08}$Co$_{3.90}$Rb$_{0.15}$ was supported on silica (metal oxide: 60% by mass, silica: 40% by mass) was produced by the following procedures.

First, 1333 g of a silica sol containing 30% by mass of SiO$_2$ was placed in a container with a lid and kept at 40° C., and 25.0 g of oxalic acid dihydrate dissolved in 287.5 g of water was added thereto with stirring at a stirring rotation speed of 120 rpm. After closing of the lid, the mixture was stirred for 10 minutes to prepare an aqueous silica solution. In another container with a lid, 476.7 g of ammonium paramolybdate [$(NH_4)_6Mo_7O_{24} \cdot 4H_2O$] was placed and dissolved in 850.8 g of warm water of 60° C. After cooling to 45° C., 35.8 g of 15% by mass of an aqueous ammonia solution was added thereto to prepare an aqueous molybdenum solution. In a further alternative container with a lid, 51.6 g of bismuth nitrate [$Bi(NO_3)_3 \cdot 5H_2O$], 96.1 g of cerium nitrate [$Ce(NO_3)_3 \cdot 6H_2O$], 171.2 g of iron nitrate [$Fe(NO_2)_2 \cdot 9H_2O$], 203.4 g of nickel nitrate [$Ni(NO_3)_2 \cdot 6H_2O$], 258.8 g of cobalt nitrate [$Co(NO_3)_2 \cdot 6H_2O$], and 5.0 g of rubidium nitrate [$RbNO_3$] were dissolved in 393.3 g of 16.6% by mass of nitric acid and kept at 40° C. to prepare an aqueous nitrate solution. The aqueous molybdenum solution was added in 1 minute to the aqueous silica solution kept at 40° C. with stirring at a stirring rotation speed of 200 rpm to obtain an aqueous silica-molybdenum solution. The obtained solution was stirred for 5 minutes and then continuously kept at 40° C., and the aqueous nitrate solution was added in 15 seconds to the aqueous silica-molybdenum solution with stirring at a stirring rotation speed of 250 rpm to prepare a starting material slurry. The starting material slurry was stirred at 40° C. for 45 minutes while covered with the lid to prepare a catalyst precursor slurry comprising a liquid phase and a solid phase. The aggregation of metal primary particles and silica particles was able to be observed by extracting aggregates in the catalyst precursor slurry onto a replica film by the freeze-fracture replica method, and carrying out SEM measurement. In this operation, EDX measurement was able to be used in combination therewith to confirm that the particles constituting the aggregates were metal and silica. The obtained catalyst precursor slurry was used in measurement as described above to reveal that % by mass of the aggregates in the catalyst precursor slurry was 16.6% by mass, the true density of the aggregates was 2.7 g/mL, and the permittivity of the aggregate was 6. The attenuation spectrum of the catalyst precursor slurry measured by the ultrasonic attenuation method using AcoustoSizer IIX from Kyowa Interface Science Co., Ltd. was analyzed using these parameters. As a result, the average particle size of the metal primary particles constituting the aggregates was calculated as 52 nm. The range of the particle sizes of the metal primary particles was 1 μm or smaller. The obtained catalyst precursor slurry was dried using a rotary disc-type spray dryer to obtain dry particles. In this operation, the air temperature at the dryer inlet was set to 230° C., and the air temperature at the outlet was set to 110° C. The rotation speed of the disc was set to 12500 rpm. The obtained dry particles were kept at 200° C. for 5 minutes, heated at 2.5° C./min from 200° C. to 450° C., and kept at 450° C. for 20 minutes for denitration. The denitrated dry particles were calcined at 595° C. for 2 hours to obtain a catalyst for ammoxidation. The obtained catalyst for ammoxidation was supplied to a fluidized reaction vessel in advance. While the catalyst was circulated in the fluidized reaction vessel, propylene, molecular oxygen, and ammonia were reacted (ammoxidation reaction) to produce acrylonitrile. An ammonia/propylene molar ratio (N/C), an air/propylene molar ratio (A/C), and an acrylonitrile yield were determined. The results are shown in Table 1.

Example 5

A catalyst in which a metal oxide having metal component composition represented by $Mo_{12.00}Bi_{0.47}Ce_{0.99}Fe_{1.88}Ni_{3.08}Co_{3.90}Rb_{0.15}$ was supported on silica (metal oxide: 60% by mass, silica: 40% by mass) was produced by the following procedures.

First, 1333 g of a silica sol containing 30% by mass of $SiO_2$ was placed in a container with a lid and kept at 40° C., and 25.0 g of oxalic acid dihydrate dissolved in 287.5 g of water was added thereto with stirring at a stirring rotation speed of 120 rpm. After closing of the lid, the mixture was stirred for 10 minutes to prepare an aqueous silica solution. In another container with a lid, 476.7 g of ammonium paramolybdate [$(NH_4)_6Mo_7O_{24} \cdot 4H_2O$] was placed and dissolved in 850.8 g of warm water of 60° C. After cooling to 45° C., 35.8 g of 15% by mass of an aqueous ammonia solution was added thereto to prepare an aqueous molybdenum solution. In a further alternative container with a lid, 51.6 g of bismuth nitrate [$Bi(NO_3)_3 \cdot 5H_2O$], 96.1 g of cerium nitrate [$Ce(NO_3)_3 \cdot 6H_2O$], 171.2 g of iron nitrate [$Fe(NO_3)_3 \cdot 9H_2O$], 203.4 g of nickel nitrate [$Ni(NO_3)_2 \cdot 6H_2O$], 258.8 g of cobalt nitrate [$Co(NO_3)_2 \cdot 6H_2O$], and 5.0 g of rubidium nitrate [$RbNO_3$] were dissolved in 393.3 g of 16.6% by mass of nitric acid and kept at 40° C. to prepare an aqueous nitrate solution. The aqueous molybdenum solution was added in 1 minute to the aqueous silica solution kept at 40° C. with stirring at a stirring rotation speed of 200 rpm to obtain an aqueous silica-molybdenum solution. The obtained solution was stirred for 5 minutes and then continuously kept at 40° C., and the aqueous nitrate solution was added in 75 seconds to the aqueous silica-molybdenum solution with stirring at a stirring rotation speed of 250 rpm to prepare a starting material slurry. The starting material slurry was stirred at 40° C. for 45 minutes while covered with the lid to prepare a catalyst precursor slurry comprising a liquid phase and a solid phase. The aggregation of metal primary particles and silica particles was able to be observed by extracting aggregates in the catalyst precursor slurry onto a replica film by the freeze-fracture replica method, and carrying out SEM measurement. In this operation, EDX measurement was able to be used in combination therewith to confirm that the particles constituting the aggregates were metal and silica. The obtained catalyst precursor slurry was used in measurement as described above to reveal that % by mass of the aggregates in the catalyst precursor slurry was 16.6% by mass, the true density of the aggregates was 2.7 g/mL, and the permittivity of the aggregate was 6. The attenuation spectrum of the catalyst precursor slurry measured by the ultrasonic attenuation method using AcoustoSizer IIX from Kyowa Interface Science Co., Ltd. was analyzed using these parameters. As a result, the average particle size of the metal primary particles constituting the aggregates was calculated as 67 nm. The range of the particle sizes of the metal primary particles was 1 μm or smaller. The obtained catalyst precursor slurry was dried using a rotary disc-type spray dryer to obtain dry particles. In this operation, the air temperature at the dryer inlet was set to 230° C., and the air temperature at the outlet was set to 110° C. The rotation speed of the disc was set to 12500 rpm. The obtained dry particles were kept at 200° C. for 5 minutes, heated at 2.5° C./min from 200° C. to 450° C., and kept at 450° C. for 20 minutes for denitration. The denitrated dry particles were calcined at 595° C. for 2 hours to obtain a catalyst for ammoxidation. The obtained catalyst for ammoxidation was supplied to a fluidized reaction vessel in advance. While the catalyst was circulated in the fluidized reaction vessel, propylene, molecular oxygen, and ammonia were reacted (ammoxidation reaction) to produce acrylonitrile. An ammonia/propylene molar ratio (N/C), an air/propylene molar ratio (A/C), and an acrylonitrile yield were determined. The results are shown in Table 1.

Example 6

A catalyst in which a metal oxide having metal component composition represented by $Mo_{12.00}Bi_{0.47}Ce_{0.99}Fe_{1.88}Ni_{3.08}Co_{3.90}Rb_{0.15}$ was supported on silica (metal oxide: 60% by mass, silica: 40% by mass) was produced by the following procedures.

First, 667 g of a silica sol containing 30% by mass of $SiO_2$ was placed in a container with a lid and kept at 40° C., and 12.5 g of oxalic acid dihydrate dissolved in 143.8 g of water was added thereto with stirring at a stirring rotation speed of 120 rpm. After closing of the lid, the mixture was stirred for 10 minutes to prepare an aqueous silica solution. In another container with a lid, 238.3 g of ammonium paramolybdate $[(NH_4)_6Mo_7O_{24}\cdot 4H_2O]$ was placed and dissolved in 1310.8 g of warm water of 60° C. After cooling to 45° C., 17.8 g of 15% by mass of an aqueous ammonia solution was added thereto to prepare an aqueous molybdenum solution. In a further alternative container with a lid, 25.8 g of bismuth nitrate $[Bi(NO_3)_3\cdot 5H_2O]$, 48.0 g of cerium nitrate $[Ce(NO_3)_3\cdot 6H_2O]$, 85.6 g of iron nitrate $[Fe(NO_3)_3\cdot 9H_2O]$, 101.6 g of nickel nitrate $[Ni(NO_3)_2\cdot 6H_2O]$, 129.4 g of cobalt nitrate $[Co(NO_3)_2\cdot 6H_2O]$, and 2.5 g of rubidium nitrate $[RbNO_3]$ were dissolved in 297.65 g of 16.6% by mass of nitric acid and kept at 40° C. to prepare an aqueous nitrate solution. The aqueous molybdenum solution was added in 1 minute to the aqueous silica solution kept at 40° C. with stirring at a stirring rotation speed of 200 rpm to obtain an aqueous silica-molybdenum solution. The obtained solution was stirred for 5 minutes and then continuously kept at 40° C., and the aqueous nitrate solution was added in 1 minute to the aqueous silica-molybdenum solution with stirring at a stirring rotation speed of 250 rpm to prepare a starting material slurry. The starting material slurry was stirred at 40° C. for 45 minutes while covered with the lid to prepare a catalyst precursor slurry comprising a liquid phase and a solid phase. The aggregation of metal primary particles and silica particles was able to be observed by extracting aggregates in the catalyst precursor slurry onto a replica film by the freeze-fracture replica method, and carrying out SEM measurement. In this operation, EDX measurement was able to be used in combination therewith to confirm that the particles constituting the aggregates were metal and silica. The obtained catalyst precursor slurry was used in measurement as described above to reveal that % by mass of the aggregates in the catalyst precursor slurry was 10.6% by mass, the true density of the aggregates was 2.7 g/mL, and the permittivity of the aggregate was 6. The attenuation spectrum of the catalyst precursor slurry measured by the ultrasonic attenuation method using AcoustoSizer IIX from Kyowa Interface Science Co., Ltd. was analyzed using these parameters. As a result, the average particle size of the metal primary particles constituting the aggregates was calculated as 55 nm. The range of the particle sizes of the metal primary particles was 1 μm or smaller. The obtained catalyst precursor slurry was dried using a rotary disc-type spray dryer to obtain dry particles. In this operation, the air temperature at the dryer inlet was set to 230° C., and the air temperature at the outlet was set to 110° C. The rotation speed of the disc was set to 12500 rpm. The obtained dry particles were kept at 200° C. for 5 minutes, heated at 2.5° C./min from 200° C. to 450° C., and kept at 450° C. for 20 minutes for denitration. The denitrated dry particles were calcined at 605° C. for 2 hours to obtain a catalyst for ammoxidation. The obtained catalyst for ammoxidation was supplied to a fluidized reaction vessel in advance. While the catalyst was circulated in the fluidized reaction vessel, propylene, molecular oxygen, and ammonia were reacted (ammoxidation reaction) to produce acrylonitrile. An ammonia/propylene molar ratio (N/C), an air/propylene molar ratio (A/C), and an acrylonitrile yield were determined. The results are shown in Table 1.

Example 7

A catalyst in which a metal oxide having metal component composition represented by $Mo_{12.00}Bi_{0.47}Ce_{0.99}Fe_{1.88}Ni_{3.08}Co_{3.90}Rb_{0.15}$ was supported on silica (metal oxide: 60% by mass, silica: 40% by mass) was produced by the following procedures.

First, 1333 g of a silica sol containing 30% by mass of $SiO_2$ was placed in a container with a lid and kept at 40° C., and 25.0 g of nitrilotriacetic acid dissolved in 287.5 g of water was added thereto with stirring at a stirring rotation speed of 120 rpm. After closing of the lid, the mixture was stirred for 10 minutes to prepare an aqueous silica solution. In another container with a lid, 476.7 g of ammonium paramolybdate $[(NH_4)_6Mo_2O_{24}\cdot 4H_2O]$ was placed and dissolved in 850.8 g of warm water of 60° C. After cooling to 45° C., 35.8 g of 15% by mass of an aqueous ammonia solution was added thereto to prepare an aqueous molybdenum solution. In a further alternative container with a lid, 51.6 g of bismuth nitrate $[Bi(NO_3)_3\cdot 5H_2O]$, 96.1 g of cerium nitrate $[Ce(NO_3)_3\cdot 6H_2O]$, 171.2 g of iron nitrate $[Fe(NO_3)_3\cdot 9H_2O]$, 203.4 g of nickel nitrate $[Ni(NO_3)_2\cdot 6H_2O]$, 258.8 g of cobalt nitrate $[Co(NO_3)_2\cdot 6H_2O]$, and 5.0 g of rubidium nitrate $[RbNO_3]$ were dissolved in 393.3 g of 16.6% by mass of nitric acid and kept at 40° C. to prepare an aqueous nitrate solution. The aqueous molybdenum solution was added in 1 minute to the aqueous silica solution kept at 40° C. with stirring at a stirring rotation speed of 200 rpm to obtain an aqueous silica-molybdenum solution. The obtained solution was stirred for 5 minutes and then continuously kept at 40° C., and the aqueous nitrate solution was added in 1 minute to the aqueous silica-molybdenum solution with stirring at a stirring rotation speed of 250 rpm to prepare a starting material slurry. The starting material slurry was stirred at 40° C. for 45 minutes while covered with the lid to prepare a catalyst precursor slurry comprising a liquid phase and a solid phase. The aggregation of metal primary particles and silica particles was able to be observed by extracting aggregates in the catalyst precursor slurry onto a replica film by the freeze-fracture replica method, and carrying out SEM measurement. In this operation, EDX measurement was able to be used in combination therewith to confirm that the particles constituting the aggregates were metal and silica. The obtained catalyst precursor slurry was used in measurement as described above to reveal that % by mass of the aggregates in the catalyst precursor slurry was 21.7% by mass, the true density of the aggregates was 2.7 g/mL, and the permittivity of the aggregate was 6. The attenuation spectrum of the catalyst precursor slurry measured by the ultrasonic attenuation method using AcoustoSizer IIX from Kyowa Interface Science Co., Ltd. was analyzed using these parameters. As a result, the average particle size of the metal primary particles constituting the aggregates was calculated as 55 nm. The range of the particle sizes of the metal primary particles was 1 μm or smaller. The obtained catalyst precursor slurry was dried using a rotary disc-type spray dryer to obtain dry particles. In this operation, the air temperature at the dryer inlet was set to 230° C., and the air temperature at the outlet was set to 110° C. The rotation speed of the disc was set to 12500 rpm. The obtained dry particles were kept at 200° C. for 5 minutes, heated at 2.5° C./min from 200° C.

to 450° C., and kept at 450° C. for 20 minutes for denitration. The denitrated dry particles were calcined at 595° C. for 2 hours to obtain a catalyst for ammoxidation. The obtained catalyst for ammoxidation was supplied to a fluidized reaction vessel in advance. While the catalyst was circulated in the fluidized reaction vessel, propylene, molecular oxygen, and ammonia were reacted (ammoxidation reaction) to produce acrylonitrile. An ammonia/propylene molar ratio (N/C), an air/propylene molar ratio (A/C), and an acrylonitrile yield were determined. The results are shown in Table 1.

Example 8

A catalyst in which a metal oxide having metal component composition represented by $Mo_{12.00}Bi_{0.47}Ce_{0.99}Fe_{1.88}Ni_{3.08}CO_{3.90}Rb_{0.15}$ was supported on silica (metal oxide: 60% by mass, silica: 40% by mass) was produced by the following procedures.

First, 1333 g of a silica sol containing 30% by mass of $SiO_2$ was placed in a container with a lid and kept at 40° C., and 25.0 g of oxalic acid dissolved in 287.5 g of water was added thereto with stirring at a stirring rotation speed of 120 rpm. After closing of the lid, the mixture was stirred for 10 minutes to prepare an aqueous silica solution. In another container with a lid, 476.7 g of ammonium paramolybdate $[(NH_4)_6Mo_7O_{24}.4H_2O]$ was placed and dissolved in 850.8 g of warm water of 60° C. After cooling to 45° C., 35.8 g of 15% by mass of an aqueous ammonia solution was added thereto to prepare an aqueous molybdenum solution. In a further alternative container with a lid, 51.6 g of bismuth nitrate $[Bi(NO_3)_3.5H_2O]$, 96.1 g of cerium nitrate $[Ce(NO_3)_3.6H_2O]$, 171.2 g of iron nitrate $[Fe(NO_3)_3.9H_2O]$, 203.4 g of nickel nitrate $[Ni(NO_3)_2.6H_2O]$, 258.8 g of cobalt nitrate $[Co(NO_3)_2.6H_2O]$, and 5.0 g of rubidium nitrate $[RbNO_3]$ were dissolved in 393.3 g of 16.6% by mass of nitric acid and kept at 40° C. to prepare an aqueous nitrate solution. The aqueous molybdenum solution was added in 1 minute to the aqueous silica solution kept at 40° C. with stirring at a stirring rotation speed of 200 rpm to obtain an aqueous silica-molybdenum solution. The obtained solution was stirred for 5 minutes and then continuously kept at 40° C., and the aqueous nitrate solution was added in 1 minute to the aqueous silica-molybdenum solution with stirring at a stirring rotation speed of 250 rpm to prepare a starting material slurry. The starting material slurry was stirred at 40° C. for 45 minutes while covered with the lid, and further, 20 g of 28% by mass of an aqueous ammonia solution was added thereto to prepare a catalyst precursor slurry comprising a liquid phase and a solid phase. The aggregation of metal primary particles and silica particles was able to be observed by extracting aggregates in the catalyst precursor slurry onto a replica film by the freeze-fracture replica method, and carrying out SEM measurement. In this operation, EDX measurement was able to be used in combination therewith to confirm that the particles constituting the aggregates were metal and silica. The obtained catalyst precursor slurry was used in measurement as described above to reveal that % by mass of the aggregates in the catalyst precursor slurry was 19.0% by mass, the true density of the aggregates was 2.7 g/mL, and the permittivity of the aggregate was 6. The attenuation spectrum of the catalyst precursor slurry measured by the ultrasonic attenuation method using AcoustoSizer IIX from Kyowa Interface Science Co., Ltd. was analyzed using these parameters. As a result, the average particle size of the metal primary particles constituting the aggregates was calculated as 97 nm. The range of the particle sizes of the metal primary particles was 1 μm or smaller. The obtained catalyst precursor slurry was dried using a rotary disc-type spray dryer to obtain dry particles. In this operation, the air temperature at the dryer inlet was set to 230° C., and the air temperature at the outlet was set to 110° C. The rotation speed of the disc was set to 12500 rpm. The obtained dry particles were kept at 200° C. for 5 minutes, heated at 2.5° C./min from 200° C. to 450° C., and kept at 450° C. for 20 minutes for denitration. The denitrated dry particles were calcined at 590° C. for 2 hours to obtain a catalyst for ammoxidation. The obtained catalyst for ammoxidation was supplied to a fluidized reaction vessel in advance. While the catalyst was circulated in the fluidized reaction vessel, propylene, molecular oxygen, and ammonia were reacted (ammoxidation reaction) to produce acrylonitrile. An ammonia/propylene molar ratio (N/C), an air/propylene molar ratio (A/C), and an acrylonitrile yield were determined. The results are shown in Table 1.

Example 9

A catalyst in which a metal oxide having metal component composition represented by $Mo_{12.00}Bi_{0.47}Ce_{0.99}Fe_{1.88}Ni_{3.08}CO_{3.90}Rb_{0.15}$ was supported on silica (metal oxide: 60% by mass, silica: 40% by mass) was produced by the following procedures.

First, 1333 g of a silica sol containing 30% by mass of $SiO_2$ was placed in a container with a lid and kept at 40° C., and 25.0 g of oxalic acid dissolved in 287.5 g of water was added thereto with stirring at a stirring rotation speed of 120 rpm. After closing of the lid, the mixture was stirred for 10 minutes to prepare an aqueous silica solution. In another container with a lid, 476.7 g of ammonium paramolybdate $[(NH_4)_6Mo_7O_{24}.4H_2O]$ was placed and dissolved in 850.8 g of warm water of 60° C. After cooling to 45° C., 35.8 g of 15% by mass of an aqueous ammonia solution was added thereto to prepare an aqueous molybdenum solution. In a further alternative container with a lid, 51.6 g of bismuth nitrate $[Bi(NO_3)_3.5H_2O]$, 96.1 g of cerium nitrate $[Ce(NO_3)_3.6H_2O]$, 171.2 g of iron nitrate $[Fe(NO_3)_3.9H_2O]$, 203.4 g of nickel nitrate $[Ni(NO_3)_2.6H_2O]$, 258.8 g of cobalt nitrate $[Co(NO_3)_2.6H_2O]$, and 5.0 g of rubidium nitrate $[RbNO_3]$ were dissolved in 393.3 g of 16.6% by mass of nitric acid and kept at 40° C. to prepare an aqueous nitrate solution. The aqueous molybdenum solution was added in 1 minute to the aqueous silica solution kept at 40° C. with stirring at a stirring rotation speed of 200 rpm to obtain an aqueous silica-molybdenum solution. The obtained solution was stirred for 5 minutes and then continuously kept at 40° C., and the aqueous nitrate solution was added in 1 minute to the aqueous silica-molybdenum solution with stirring at a stirring rotation speed of 250 rpm to prepare a starting material slurry. The starting material slurry was stirred at 40° C. for 45 minutes while covered with the lid, and further, 28 g of 28% by mass of an aqueous ammonia solution was added thereto to prepare a catalyst precursor slurry comprising a liquid phase and a solid phase. The aggregation of metal primary particles and silica particles was able to be observed by extracting aggregates in the catalyst precursor slurry onto a replica film by the freeze-fracture replica method, and carrying out SEM measurement. In this operation, EDX measurement was able to be used in combination therewith to confirm that the particles constituting the aggregates were metal and silica. The obtained catalyst precursor slurry was used in measurement as described above to reveal that % by mass of the aggregates in the catalyst precursor slurry was 22.5% by mass, the true density of the aggregates was 2.7 g/mL, and the permittivity of the aggregate was 6. The attenuation spectrum of the catalyst precursor slurry measured by the ultrasonic attenuation method using AcoustoSizer IIX from Kyowa Interface Science Co., Ltd. was analyzed using these parameters. As a result, the average particle size of the metal primary particles constituting the aggregates was calculated as 123 nm. The range of the particle sizes of the metal primary particles was 1 μm or smaller. The obtained catalyst precursor slurry was dried using a rotary disc-type spray dryer to obtain dry particles. In this operation, the air temperature at the dryer inlet was set to 230° C., and the air temperature at the outlet was set to 110° C. The rotation speed of the disc was set to 12500 rpm. The obtained dry particles were kept at 200° C. for 5 minutes, heated at 2.5° C./min from 200° C. to 450° C., and kept at 450° C. for 20 minutes for denitration. The denitrated dry particles were calcined at 590° C. for 2 hours to obtain a catalyst for ammoxidation. The obtained catalyst for ammoxidation was supplied to a fluidized reaction vessel in advance. While the catalyst was circulated in the fluidized reaction vessel, propylene, molecular oxygen, and ammonia were reacted (ammoxidation reaction) to produce acrylonitrile. An ammonia/propylene molar ratio (N/C), an air/propylene molar ratio (A/C), and an acrylonitrile yield were determined. The results are shown in Table 1.

Example 10

A catalyst in which a metal oxide having metal component composition represented by $Mo_{12.00}Bi_{0.47}Ce_{0.99}Fe_{1.88}Ni_{3.08}Co_{3.90}Rb_{0.15}$ was supported on silica (metal oxide: 60% by mass, silica: 40% by mass) was produced by the following procedures.

First, 1333 g of a silica sol containing 30% by mass of $SiO_2$ was placed in a container with a lid and kept at 40° C., and 25.0 g of oxalic acid dihydrate dissolved in 287.5 g of water was added thereto with stirring at a stirring rotation speed of 120 rpm. After closing of the lid, the mixture was stirred for 10 minutes to prepare an aqueous silica solution. In another container with a lid, 476.7 g of ammonium paramolybdate $[(NH_4)_6Mo_2O_{24}\cdot 4H_2O]$ was placed and dissolved in 850.8 g of warm water of 60° C. After cooling to 45° C., 35.8 g of 15% by mass of an aqueous ammonia solution was added thereto to prepare an aqueous molybdenum solution. In a further alternative container with a lid, 51.6 g of bismuth nitrate $[Bi(NO_3)_3\cdot 5H_2O]$, 96.1 g of cerium nitrate $[Ce(NO_3)_3\cdot 6H_2O]$, 171.2 g of iron nitrate $[Fe(NO_2)_2\cdot 9H_2O]$, 203.4 g of nickel nitrate $[Ni(NO_3)_2\cdot 6H_2O]$, 258.8 g of cobalt nitrate $[Co(NO_3)_2\cdot 6H_2O]$, and 5.0 g of rubidium nitrate $[RbNO_3]$ were dissolved in 393.3 g of 16.6% by mass of nitric acid and kept at 40° C. to prepare an aqueous nitrate solution. The aqueous molybdenum solution was added in 1 minute to the aqueous silica solution kept at 40° C. with stirring at a stirring rotation speed of 150 rpm to obtain an aqueous silica-molybdenum solution. The obtained solution was stirred for 5 minutes and then continuously kept at 40° C., and the aqueous nitrate solution was added in 1 minute to the aqueous silica-molybdenum solution with stirring at a stirring rotation speed of 160 rpm to prepare a starting material slurry. The starting material slurry was stirred at 40° C. for 45 minutes while covered with the lid to prepare a catalyst precursor slurry comprising a liquid phase and a solid phase. The aggregation of metal primary particles and silica particles was able to be observed by extracting aggregates in the catalyst precursor slurry onto a replica film by the freeze-fracture replica method, and carrying out SEM measurement. In this operation, EDX measurement was able to be used in combination therewith to confirm that the particles constituting the aggregates were metal and silica. The obtained catalyst precursor slurry was used in measurement as described above to reveal that % by mass of the aggregates in the catalyst precursor slurry was 16.1% by mass, the true density of the aggregates was 2.7 g/mL, and the permittivity of the aggregate was 6. The attenuation spectrum of the catalyst precursor slurry measured by the ultrasonic attenuation method using AcoustoSizer IIX from Kyowa Interface Science Co., Ltd. was analyzed using these parameters. As a result, the average particle size of the metal primary particles constituting the aggregates was calculated as 183 nm.

The range of the particle sizes of the metal primary particles was 1 μm or smaller.

The obtained catalyst precursor slurry was dried using a rotary disc-type spray dryer to obtain dry particles. In this operation, the air temperature at the dryer inlet was set to 230° C., and the air temperature at the outlet was set to 110° C. The rotation speed of the disc was set to 12500 rpm. The obtained dry particles were kept at 200° C. for 5 minutes, heated at 2.5° C./min from 200° C. to 450° C., and kept at 450° C. for 20 minutes for denitration. The denitrated dry particles were calcined at 595° C. for 2 hours to obtain a catalyst for ammoxidation. The obtained catalyst for ammoxidation was supplied to a fluidized reaction vessel in advance. While the catalyst was circulated in the fluidized reaction vessel, propylene, molecular oxygen, and ammonia were reacted (ammoxidation reaction) to produce acrylonitrile. An ammonia/propylene molar ratio (N/C), an air/propylene molar ratio (A/C), and an acrylonitrile yield were determined. The results are shown in Table 1.

Example 11

A catalyst in which a metal oxide having metal component composition represented by $Mo_{12.00}Bi_{0.47}Ce_{0.99}Fe_{1.88}Ni_{3.08}Co_{3.90}Rb_{0.15}$ was supported on silica (metal oxide: 60% by mass, silica: 40% by mass) was produced by the following procedures.

First, 1333 g of a silica sol containing 30% by mass of $SiO_2$ was placed in a container with a lid and kept at 40° C. to prepare an aqueous silica solution. In another container with a lid, 476.7 g of ammonium paramolybdate $[(NH_4)_6Mo_7O_{24}\cdot 4H_2O]$ was placed and dissolved in 850.8 g of warm water of 60° C. After cooling to 45° C., 35.8 g of 15% by mass of an aqueous ammonia solution was added thereto to prepare an aqueous molybdenum solution. In a further alternative container with a lid, 51.6 g of bismuth nitrate $[Bi(NO_3)_3\cdot 5H_2O]$, 96.1 g of cerium nitrate $[Ce(NO_3)_3\cdot 6H_2O]$, 171.2 g of iron nitrate $[Fe(NO_3)_3\cdot 9H_2O]$, 203.4 g of nickel nitrate $[Ni(NO_3)_2\cdot 6H_2O]$, 258.8 g of cobalt nitrate $[Co(NO_3)_2\cdot 6H_2O]$, and 5.0 g of rubidium nitrate $[RbNO_3]$ were dissolved in 393.3 g of 16.6% by mass of nitric acid and kept at 40° C. to prepare an aqueous nitrate solution. The aqueous molybdenum solution was added in 1 minute to the aqueous silica solution kept at 40° C. with stirring at a stirring rotation speed of 120 rpm to obtain an aqueous silica-molybdenum solution. The obtained solution was stirred for 5 minutes and then continuously kept at 40° C., and the aqueous nitrate solution was added in 1 minute to the aqueous silica-molybdenum solution with stirring at a stirring rotation speed of 150 rpm to prepare a starting material slurry. The starting material slurry was stirred at 40° C. for 45 minutes while covered with the lid to prepare a catalyst precursor slurry comprising a liquid phase and a solid phase. The aggregation of metal primary particles and silica particles was able to be observed by extracting aggregates in the catalyst precursor slurry onto a replica film by the freeze-fracture replica method, and carrying out SEM measurement. In this operation, EDX measurement was able to be used in combination therewith to confirm that the particles constituting the aggregates were metal and silica. The obtained catalyst precursor slurry was used in measurement as described above to reveal that % by mass of the aggregates in the catalyst precursor slurry was 16.1% by mass, the true density of the aggregates was 2.7 g/mL, and the permittivity of the aggregate was 6. The attenuation spectrum of the catalyst precursor slurry measured by the ultrasonic attenuation method using AcoustoSizer IIX from Kyowa Interface Science Co., Ltd. was analyzed using these parameters. As a result, the average particle size of the metal primary particles constituting the aggregates was calculated as 188 nm. The range of the particle sizes of the metal primary particles was 1 μm or smaller.

The obtained catalyst precursor slurry was dried using a rotary disc-type spray dryer to obtain dry particles. In this operation, the air temperature at the dryer inlet was set to 230° C., and the air temperature at the outlet was set to 110° C. The rotation speed of the disc was set to 12500 rpm. The obtained dry particles were kept at 200° C. for 5 minutes, heated at 2.5° C./min from 200° C. to 450° C., and kept at 450° C. for 20 minutes for denitration. The denitrated dry particles were calcined at 595° C. for 2 hours to obtain a catalyst for ammoxidation. The obtained catalyst for ammoxidation was supplied to a fluidized reaction vessel in advance. While the catalyst was circulated in the fluidized reaction vessel, propylene, molecular oxygen, and ammonia were reacted (ammoxidation reaction) to produce acrylonitrile. An ammonia/propylene molar ratio (N/C), an air/propylene molar ratio (A/C), and an acrylonitrile yield were determined. The results are shown in Table 1.

Example 12

A catalyst in which a metal oxide having metal component composition represented by $Mo_{12.00}Bi_{0.47}Ce_{0.99}Fe_{1.88}Ni_{3.08}Co_{3.90}Rb_{0.15}$ was supported on silica (metal oxide: 60% by mass, silica: 40% by mass) was produced by the following procedures.

First, 1333 g of a silica sol containing 30% by mass of $SiO_2$ was placed in a container with a lid and kept at 40° C., and 25.0 g of oxalic acid dihydrate dissolved in 287.5 g of water was added thereto with stirring at a stirring rotation speed of 120 rpm. After closing of the lid, the mixture was stirred for 10 minutes to prepare an aqueous silica solution. In another container with a lid, 476.7 g of ammonium paramolybdate $[(NH_4)_6Mo_7O_{24}\cdot 4H_2O]$ was placed and dissolved in 850.8 g of warm water of 60° C. After cooling to 45° C., 35.8 g of 15% by mass of an aqueous ammonia solution was added thereto to prepare an aqueous molybdenum solution. In a further alternative container with a lid, 51.6 g of bismuth nitrate $[Bi(NO_3)_3\cdot 5H_2O]$, 96.1 g of cerium nitrate $[Ce(NO_3)_3\cdot 6H_2O]$, 171.2 g of iron nitrate $[Fe(NO_3)_3\cdot 9H_2O]$, 203.4 g of nickel nitrate $[Ni(NO_3)_2\cdot 6H_2O]$, 258.8 g of cobalt nitrate $[Co(NO_3)_2\cdot 6H_2O]$, and 5.0 g of rubidium nitrate $[RbNO_3]$ were dissolved in 393.3 g of 16.6% by mass of nitric acid and kept at 40° C. to prepare an aqueous nitrate solution. The aqueous molybdenum solution was added in 1 minute to the aqueous silica solution kept at 40° C. with stirring at a stirring rotation speed of 180 rpm to obtain an aqueous silica-molybdenum solution. The obtained solution was stirred for 5 minutes and then continuously kept at 40° C., and the aqueous nitrate solution was added in 1 minute to the aqueous silica-molybdenum solution with stirring at a stirring rotation speed of 200 rpm to prepare a starting material slurry. The starting material slurry was stirred at 40° C. for 45 minutes while covered with the lid to prepare a catalyst precursor slurry comprising a liquid phase and a solid phase. The aggregation of metal primary particles and silica particles was able to be observed by extracting aggregates in the catalyst precursor slurry onto a replica film by the freeze-fracture replica method, and carrying out SEM measurement. In this operation, EDX measurement was able to be used in combination therewith to confirm that the particles constituting the aggregates were metal and silica. The obtained catalyst precursor slurry was used in measurement as described above to reveal that % by mass of the aggregates in the catalyst precursor slurry was 16.6% by mass, the true density of the aggregates was 2.7 g/mL, and the permittivity of the aggregate was 6. The attenuation spectrum of the catalyst precursor slurry measured by the ultrasonic attenuation method using AcoustoSizer IIX from Kyowa Interface Science Co., Ltd. was analyzed using these parameters. As a result, the average particle size of the metal primary particles constituting the aggregates was calculated as 176 nm. The range of the particle sizes of the metal primary particles was 1 μm or smaller. The obtained catalyst precursor slurry was dried using a rotary disc-type spray dryer to obtain dry particles. In this operation, the air temperature at the dryer inlet was set to 230° C., and the air temperature at the outlet was set to 110° C. The rotation speed of the disc was set to 12500 rpm. The obtained dry particles were kept at 200° C. for 5 minutes, heated at 2.5° C./min from 200° C. to 450° C., and kept at 450° C. for 20 minutes for denitration. The denitrated dry particles were calcined at 595° C. for 2 hours to obtain a catalyst for ammoxidation. The obtained catalyst for ammoxidation was supplied to a fluidized reaction vessel in advance. While the catalyst was circulated in the fluidized reaction vessel, propylene, molecular oxygen, and ammonia were reacted (ammoxidation reaction) to produce acrylonitrile. An ammonia/propylene molar ratio (N/C), an air/propylene molar ratio (A/C), and an acrylonitrile yield were determined. The results are shown in Table 1.

Comparative Example 1

A catalyst in which a metal oxide having metal component composition represented by $Mo_{12.00}Bi_{0.47}Ce_{0.99}Fe_{1.88}Ni_{3.08}Co_{3.90}Rb_{0.15}$ was supported on silica (metal oxide: 60% by mass, silica: 40% by mass) was produced by the following procedures.

First, 1333 g of a silica sol containing 30% by mass of $SiO_2$ was placed in a container with a lid and kept at 40° C., and 25.0 g of oxalic acid dihydrate dissolved in 287.5 g of water was added thereto with stirring at a stirring rotation speed of 120 rpm. After closing of the lid, the mixture was stirred for 10 minutes to prepare an aqueous silica solution. In another container with a lid, 476.7 g of ammonium paramolybdate $[(NH_4)_6Mo_2O_{24}\cdot 4H_2O]$ was placed and dissolved in 850.8 g of warm water of 60° C. After cooling to 45° C., 35.8 g of 15% by mass of an aqueous ammonia solution was added thereto to prepare an aqueous molybdenum solution. In a further alternative container with a lid, 51.6 g of bismuth nitrate $[Bi(NO_3)_3\cdot 5H_2O]$, 96.1 g of cerium nitrate $[Ce(NO_3)_3\cdot 6H_2O]$, 171.2 g of iron nitrate $[Fe(NO_3)_3\cdot 9H_2O]$, 203.4 g of nickel nitrate $[Ni(NO_3)_2\cdot 6H_2O]$, 258.8 g of cobalt nitrate $[Co(NO_3)_2\cdot 6H_2O]$, and 5.0 g of rubidium nitrate $[RbNO_3]$ were dissolved in 393.3 g of 16.6% by mass of nitric acid and kept at 40° C. to prepare an aqueous nitrate solution. The aqueous molybdenum solution was added in 1 minute to the aqueous silica solution kept at 40° C. with stirring at a stirring rotation speed of 120 rpm to obtain an aqueous silica-molybdenum solution. The obtained solution was stirred for 5 minutes and then continuously kept at 40° C., and the aqueous nitrate solution was added in 1 minute to the aqueous silica-molybdenum solution with stirring at a stirring rotation speed of 120 rpm to prepare a starting material slurry. The starting material slurry was stirred at 40° C. for 45 minutes while covered with the lid to prepare a catalyst precursor slurry comprising a liquid phase and a solid phase. The aggregation of metal primary particles and silica particles was able to be observed by extracting aggregates in the catalyst precursor slurry onto a replica film by the freeze-fracture replica method, and carrying out SEM measurement. In this operation, EDX measurement was able to be used in combination therewith to confirm that the particles constituting the aggregates were metal and silica. The obtained catalyst precursor slurry was used in measurement as described above to reveal that % by mass of the aggregates in the catalyst precursor slurry was 16.1% by mass, the true density of the aggregates was 2.7 g/mL, and the permittivity of the aggregate was 6. The attenuation spectrum of the catalyst precursor slurry measured by the ultrasonic attenuation method using AcoustoSizer IIX from Kyowa Interface Science Co., Ltd. was analyzed using these parameters. As a result, the average particle size of the metal primary particles constituting the aggregates was calculated as 217 nm. The range of the particle sizes of the metal primary particles was 1 μm or smaller.

The obtained catalyst precursor slurry was dried using a rotary disc-type spray dryer to obtain dry particles. In this operation, the air temperature at the dryer inlet was set to 230° C., and the air temperature at the outlet was set to 110° C. The rotation speed of the disc was set to 12500 rpm. The obtained dry particles were kept at 200° C. for 5 minutes, heated at 2.5° C./min from 200° C. to 450° C., and kept at 450° C. for 20 minutes for denitration. The denitrated dry particles were calcined at 595° C. for 2 hours to obtain a catalyst for ammoxidation. The obtained catalyst for ammoxidation was supplied to a fluidized reaction vessel in advance. While the catalyst was circulated in the fluidized reaction vessel, propylene, molecular oxygen, and ammonia were reacted (ammoxidation reaction) to produce acrylonitrile. An ammonia/propylene molar ratio (N/C), an air/propylene molar ratio (A/C), and an acrylonitrile yield were determined. The results are shown in Table 1.

Comparative Example 2

A catalyst in which a metal oxide having metal component composition represented by $Mo_{12.00}Bi_{0.47}Ce_{0.99}Fe_{1.88}Ni_{3.08}Co_{3.90}Rb_{0.15}$ was supported on silica (metal oxide: 60% by mass, silica: 40% by mass) was produced by the following procedures.

First, 1333 g of a silica sol containing 30% by mass of $SiO_2$ was placed in a container with a lid and kept at 40° C. to prepare an aqueous silica solution. In another container with a lid, 476.7 g of ammonium paramolybdate [$(NH_4)_6Mo_7O_{24}\cdot 4H_2O$] was placed and dissolved in 850.8 g of warm water of 60° C. After cooling to 45° C., 35.8 g of 15% by mass of an aqueous ammonia solution was added thereto to prepare an aqueous molybdenum solution. In a further alternative container with a lid, 51.6 g of bismuth nitrate [$Bi(NO_3)_3\cdot 5H_2O$], 96.1 g of cerium nitrate [$Ce(NO_3)_3\cdot 6H_2O$], 171.2 g of iron nitrate [$Fe(NO_3)_3\cdot 9H_2O$], 203.4 g of nickel nitrate [$Ni(NO_3)_2\cdot 6H_2O$], 258.8 g of cobalt nitrate [$Co(NO_3)_2\cdot 6H_2O$], and 5.0 g of rubidium nitrate [$RbNO_3$] were dissolved in 393.3 g of 16.6% by mass of nitric acid and kept at 40° C. to prepare an aqueous nitrate solution. The aqueous molybdenum solution was added in 1 minute to the aqueous silica solution kept at 40° C. with stirring at a stirring rotation speed of 120 rpm to obtain an aqueous silica-molybdenum solution. The obtained solution was stirred for 5 minutes and then continuously kept at 40° C., and the aqueous nitrate solution was added in 1 minute to the aqueous silica-molybdenum solution with stirring at a stirring rotation speed of 120 rpm to prepare a starting material slurry. The starting material slurry was stirred at 40° C. for 45 minutes while covered with the lid to prepare a catalyst precursor slurry comprising a liquid phase and a solid phase. The aggregation of metal primary particles and silica particles was able to be observed by extracting aggregates in the catalyst precursor slurry onto a replica film by the freeze-fracture replica method, and carrying out SEM measurement. In this operation, EDX measurement was able to be used in combination therewith to confirm that the particles constituting the aggregates were metal and silica. The obtained catalyst precursor slurry was used in measurement as described above to reveal that % by mass of the aggregates in the catalyst precursor slurry was 16.1% by mass, the true density of the aggregates was 2.7 g/mL, and the permittivity of the aggregate was 6. The attenuation spectrum of the catalyst precursor slurry measured by the ultrasonic attenuation method using AcoustoSizer IIX from Kyowa Interface Science Co., Ltd. was analyzed using these parameters. As a result, the average particle size of the metal primary particles constituting the aggregates was calculated as 220 nm. The range of the particle sizes of the metal primary particles was 1 μm or smaller.

The obtained catalyst precursor slurry was dried using a rotary disc-type spray dryer to obtain dry particles. In this operation, the air temperature at the dryer inlet was set to 230° C., and the air temperature at the outlet was set to 110° C. The rotation speed of the disc was set to 12500 rpm. The obtained dry particles were kept at 200° C. for 5 minutes, heated at 2.5° C./min from 200° C. to 450° C., and kept at 450° C. for 20 minutes for denitration. The denitrated dry particles were calcined at 595° C. for 2 hours to obtain a catalyst for ammoxidation. The obtained catalyst for ammoxidation was supplied to a fluidized reaction vessel in advance. While the catalyst was circulated in the fluidized reaction vessel, propylene, molecular oxygen, and ammonia were reacted (ammoxidation reaction) to produce acrylonitrile. An ammonia/propylene molar ratio (N/C), an air/propylene molar ratio (A/C), and an acrylonitrile yield were determined. The results are shown in Table 1.

Comparative Example 3

A catalyst in which a metal oxide having metal component composition represented by $Mo_{12.00}Bi_{0.47}Ce_{0.99}Fe_{1.88}Ni_{3.08}Co_{3.90}Rb_{0.15}$ was supported on silica (metal oxide: 60% by mass, silica: 40% by mass) was produced by the following procedures.

First, 1333 g of a silica sol containing 30% by mass of $SiO_2$ was placed in a container with a lid and kept at 40° C., and 25.0 g of oxalic acid dihydrate dissolved in 287.5 g of water was added thereto with stirring at a stirring rotation speed of 120 rpm. After closing of the lid, the mixture was stirred for 10 minutes to prepare an aqueous silica solution. In another container with a lid, 476.7 g of ammonium paramolybdate [$(NH_4)_6Mo_2O_{24}\cdot 4H_2O$] was placed and dissolved in 850.8 g of warm water of 60° C. After cooling to 45° C., 35.8 g of 15% by mass of an aqueous ammonia solution was added thereto to prepare an aqueous molybdenum solution. In a further alternative container with a lid, 51.6 g of bismuth nitrate [Bi(NO$_3$)$_3$.5H$_2$O], 96.1 g of cerium nitrate [Ce(NO$_3$)$_3$.6H$_2$O], 171.2 g of iron nitrate [Fe(NO$_2$)$_2$.9H$_2$O], 203.4 g of nickel nitrate [Ni(NO$_3$)$_2$.6H$_2$O], 258.8 g of cobalt nitrate [Co(NO$_3$)$_2$.6H$_2$O], and 5.0 g of rubidium nitrate [RbNO$_3$] were dissolved in 393.3 g of 16.6% by mass of nitric acid and kept at 40° C. to prepare an aqueous nitrate solution. The aqueous molybdenum solution was added in 1 minute to the aqueous silica solution kept at 40° C. with stirring at a stirring rotation speed of 180 rpm to obtain an aqueous silica-molybdenum solution. The obtained solution was stirred for 5 minutes and then continuously kept at 40° C., and the aqueous nitrate solution was added in 2 minutes to the aqueous silica-molybdenum solution with stirring at a stirring rotation speed of 250 rpm to prepare a starting material slurry. The starting material slurry was stirred at 40° C. for 45 minutes while covered with the lid to prepare a catalyst precursor slurry comprising a liquid phase and a solid phase. The aggregation of metal primary particles and silica particles was able to be observed by extracting aggregates in the catalyst precursor slurry onto a replica film by the freeze-fracture replica method, and carrying out SEM measurement. In this operation, EDX measurement was able to be used in combination therewith to confirm that the particles constituting the aggregates were metal and silica. The obtained catalyst precursor slurry was used in measurement as described above to reveal that % by mass of the aggregates in the catalyst precursor slurry was 16.6% by mass, the true density of the aggregates was 2.7 g/mL, and the permittivity of the aggregate was 6. The attenuation spectrum of the catalyst precursor slurry measured by the ultrasonic attenuation method using AcoustoSizer IIX from Kyowa Interface Science Co., Ltd. was analyzed using these parameters. As a result, the average particle size of the metal primary particles constituting the aggregates was calculated as 212 nm. The range of the particle sizes of the metal primary particles was 1 μm or smaller. The obtained catalyst precursor slurry was dried using a rotary disc-type spray dryer to obtain dry particles. In this operation, the air temperature at the dryer inlet was set to 230° C., and the air temperature at the outlet was set to 110° C. The rotation speed of the disc was set to 12500 rpm. The obtained dry particles were kept at 200° C. for 5 minutes, heated at 2.5° C./min from 200° C. to 450° C., and kept at 450° C. for 20 minutes for denitration. The denitrated dry particles were calcined at 595° C. for 2 hours to obtain a catalyst for ammoxidation. The obtained catalyst for ammoxidation was supplied to a fluidized reaction vessel in advance. While the catalyst was circulated in the fluidized reaction vessel, propylene, molecular oxygen, and ammonia were reacted (ammoxidation reaction) to produce acrylonitrile. An ammonia/propylene molar ratio (N/C), an air/propylene molar ratio (A/C), and an acrylonitrile yield were determined. The results are shown in Table 1.

TABLE 1

| | Slurry preparation conditions | | | | | Results | | | | |
| --- | --- | --- | --- | --- | --- | --- | --- | --- | --- | --- |
| | | Free acid concentration (%) | Metal oxide/carrier mass ratio in catalyst powder | Mass ratio of metal starting material + carrier to whole slurry (% by mass) | Stirring power (rpm) | Time to completely add aqueous metal salt solution (sec) | about particle size Average particle size of metal primary particle (nm) | Reaction conditions and results | | |
| | Additive | | | | | | | Reaction temperature (° C.) | N/C | A/C | Acrylonitrile yield (%) |
| Example 1 | Oxalic acid | 1.08 | 60/40 | 31 | 120→200→250 | 60 | 61 | 430 | 1.18 | 8.81 | 84.0 |
| Example 2 | Oxalic acid | 1.08 | 60/40 | 31 | 120→200→275 | 60 | 57 | 430 | 1.21 | 8.88 | 84.1 |
| Example 3 | — | 1.08 | 60/40 | 31 | 200→250 | 60 | 64 | 430 | 1.20 | 8.92 | 83.7 |
| Example 4 | Oxalic acid | 1.08 | 60/40 | 31 | 120→200→250 | 15 | 52 | 430 | 1.24 | 8.95 | 84.5 |
| Example 5 | Oxalic acid | 1.08 | 60/40 | 31 | 120→200→250 | 75 | 67 | 430 | 1.23 | 9.01 | 83.5 |
| Example 6 | Oxalic acid | 1.24 | 60/40 | 18 | 120→200→250 | 60 | 55 | 430 | 1.29 | 9.18 | 83.5 |
| Example 7 | Nitrilotriacetic acid | 1.08 | 60/40 | 31 | 120→200→250 | 60 | 55 | 430 | 1.13 | 8.66 | 83.7 |
| Example 8 | Oxalic acid | 0.41 | 60/40 | 31 | 120→200→250 | 60 | 97 | 430 | 1.21 | 8.93 | 83.5 |
| Example 9 | Oxalic acid | 0.28 | 60/40 | 31 | 120→200→250 | 60 | 123 | 430 | 1.27 | 9.15 | 83.2 |
| Example 10 | Oxalic acid | 1.08 | 60/40 | 31 | 120→150→160 | 60 | 183 | 430 | 1.21 | 8.92 | 82.7 |
| Example 11 | — | 1.08 | 60/40 | 31 | 120→150 | 60 | 188 | 430 | 1.17 | 8.97 | 82.4 |
| Example 12 | Oxalic acid | 1.08 | 60/40 | 31 | 120→180→200 | 60 | 176 | 430 | 1.23 | 8.92 | 82.6 |
| Comparative Example 1 | Oxalic acid | 1.08 | 60/40 | 31 | 120→120→120 | 60 | 217 | 430 | 1.20 | 9.16 | 81.0 |
| Comparative Example 2 | — | 1.08 | 60/40 | 31 | 120→120 | 60 | 220 | 430 | 1.15 | 8.86 | 80.9 |
| Comparative Example 3 | Oxalic acid | 1.08 | 60/40 | 31 | 120→180→250 | 120 | 212 | 430 | 1.24 | 9.05 | 81.3 |

As is evident from Table 1, all the catalysts for ammoxidation obtained in Examples 1 to 12 were able to synthesize acrylonitrile with a high yield. On the other hand, the catalysts for ammoxidation obtained in Comparative Examples 1 to 3 had a low yield of acrylonitrile as compared with Examples 1 to 12, though having the same metal composition as in Examples 1 to 12.

The present application is based on the Japanese patent application filed on Aug. 23, 2018 (Japanese Patent Application No. 2018-156514), the content of which are incorporated herein by reference in their entirety.

The invention claimed is:

1. A method for producing a catalyst for ammoxidation, comprising steps of:
   preparing a catalyst precursor slurry comprising a liquid phase and a solid phase;
   drying the catalyst precursor slurry to obtain a dry particle; and
   calcining the dry particle to obtain a catalyst for ammoxidation,
   wherein the solid phase of the catalyst precursor slurry comprises an aggregate containing a metal and a support, metal primary particles constituting the aggregate have a particle size of 1 μm or smaller, and an average particle size of the metal primary particles is 40 nm or larger and 200 nm or smaller, wherein the catalyst for ammoxidation comprises a composite metal oxide having composition represented by the following general formula (1): $Mo_{12}Bi_aFe_bX_cY_dZ_eO_f$ (1) wherein X represents one or more elements selected from the group consisting of nickel, cobalt, magnesium, calcium, zinc, strontium, and barium; Y represents one or more elements selected from the group consisting of cerium, chromium, lanthanum, neodymium, yttrium, praseodymium, samarium, aluminum, gallium, and indium; Z represents one or more elements selected from the group consisting of potassium, rubidium and cesium; a represents the atomic ratio of bismuth to the 12 atoms of molybdenum and satisfies $0.1<a<2.0$; b represents the atomic ratio of iron to the 12 atoms of molybdenum and satisfies $0.1<b<3.0$; c represents the atomic ratio of X to the 12 atoms of molybdenum and satisfies $0.1<c<10.0$; d represents the atomic ratio of Y to the 12 atoms of molybdenum and satisfies $0.1<d<3.0$; e represents the atomic ratio of Z to the 12 atoms of molybdenum and satisfies $0.01<e<2.0$; and f represents the atomic ratio of oxygen to the 12 atoms of molybdenum and is the number of atoms of oxygen necessary for satisfying valence requirements of other elements present.

2. The method for producing the catalyst for ammoxidation according to claim 1, wherein in the step of preparing the catalyst precursor slurry comprising the liquid phase and the solid phase, a free acid concentration in the slurry is 0.1% or more and 1.2% or less.

3. The method for producing the catalyst for ammoxidation according to claim 1, wherein in the step of preparing the catalyst precursor slurry comprising the liquid phase and the solid phase, the free acid concentration in the slurry is 0.8% or more and 1.2% or less.

4. The method for producing the catalyst for ammoxidation according to claim 1, wherein the catalyst for ammoxidation comprises a support, and a content of the support in the catalyst for ammoxidation is 35 to 45% by mass.

5. The method for producing the catalyst for ammoxidation according to claim 1, wherein in the step of preparing the catalyst precursor slurry comprising the liquid phase and the solid phase, a proportion of a total mass of the metal component and the support as starting materials to a mass of the whole catalyst precursor slurry is 10% by mass or more and 40% by mass or less.

6. The method for producing the catalyst for ammoxidation according to claim 1, wherein in the step of preparing the catalyst precursor slurry comprising the liquid phase and the solid phase, the proportion of the total mass of the metal component and the support as starting materials to the mass of the whole catalyst precursor slurry is 20% by mass or more and 35% by mass or less.

7. The method for producing the catalyst for ammoxidation according to claim 1, wherein in the step of drying the catalyst precursor slurry to obtain the dry particle, a dryer is kept at an inlet air temperature of 180 to 250° C. and at an outlet temperature of 100 to 150° C.

8. The method for producing the catalyst for ammoxidation according to claim 1, wherein the step of calcining the dry particle to obtain the catalyst for ammoxidation comprises denitration treatment before the calcination, and the denitration treatment involves performing heating at 150 to 450° C. for 1.5 to 3 hours.

9. The method for producing the catalyst for ammoxidation according to claim 1, wherein in the step of calcining the dry particle to obtain the catalyst for ammoxidation, a calcination temperature is 550 to 650° C.

10. A method for producing acrylonitrile, comprising steps of:
    preparing a catalyst for ammoxidation by the method of claim 1; and
    supplying the catalyst for ammoxidation to a fluidized reaction vessel in advance, and while circulating the catalyst in the fluidized reaction vessel, reacting propylene, molecular oxygen, and ammonia to obtain acrylonitrile,
    wherein the solid phase of the catalyst precursor slurry comprises an aggregate containing a metal and a support, metal primary particles constituting the aggregate have a particle size of 1 μm or smaller, and an average particle size of the metal primary particles is 40 nm or larger and 200 nm or smaller.

11. The method for producing acrylonitrile according to claim 10, wherein
    a source of the molecular oxygen is air, and
    a molar ratio of ammonia and air to propylene is in the range of 1/(0.8 to 1.4)/(7 to 12) in terms of a ratio of propylene/ammonia/air.

12. The method for producing acrylonitrile according to claim 10, wherein
    a source of the molecular oxygen is air, and
    a molar ratio of ammonia and air to propylene is in the range of 1/(0.9 to 1.3)/(8 to 11) in terms of a ratio of propylene/ammonia/air.

13. The method for producing acrylonitrile according to claim 10, wherein a temperature at which propylene, molecular oxygen, and ammonia are reacted in the presence of the catalyst for ammoxidation is in the range of 350 to 550° C.

14. The method for producing acrylonitrile according to claim 10, wherein a temperature at which propylene, molecular oxygen, and ammonia are reacted in the presence of the catalyst for ammoxidation is in the range of 400 to 500° C.

15. The method for producing acrylonitrile according to claim 10, wherein in the step of preparing the catalyst precursor slurry comprising the liquid phase and the solid phase, a free acid concentration in the slurry is 0.1% or more and 1.2% or less.

16. The method for producing acrylonitrile according to claim 10, wherein in the step of preparing the catalyst precursor slurry comprising the liquid phase and the solid phase, the free acid concentration in the slurry is 0.8% or more and 1.2% or less.

17. The method for producing acrylonitrile according to claim 10, wherein the catalyst for ammoxidation comprises a support, and a content of the support in the catalyst for ammoxidation is 35 to 45% by mass.

18. The method for producing acrylonitrile according to claim 10, wherein in the step of preparing the catalyst precursor slurry comprising the liquid phase and the solid phase, a proportion of a total mass of the metal component and the support as starting materials to a mass of the whole catalyst precursor slurry is 10% by mass or more and 40% by mass or less.

19. The method for producing acrylonitrile according to claim 10, wherein in the step of preparing the catalyst precursor slurry comprising the liquid phase and the solid phase, the proportion of the total mass of the metal component and the support as starting materials to the mass of the whole catalyst precursor slurry is 20% by mass or more and 35% by mass or less.

20. The method for producing acrylonitrile according to claim 10, wherein in the step of drying the catalyst precursor slurry to obtain the dry particle, a dryer is kept at an inlet air temperature of 180 to 250° C. and at an outlet temperature of 100 to 150° C.

21. The method for producing acrylonitrile according to claim 10, wherein the step of calcining the dry particle to obtain the catalyst for ammoxidation comprises denitration treatment before the calcination, and the denitration treatment involves performing heating at 150 to 450° C. for 1.5 to 3 hours.

22. The method for producing acrylonitrile according to claim 10, wherein in the step of calcining the dry particle to obtain the catalyst for ammoxidation, a calcination temperature is 550 to 650° C.

\* \* \* \* \*